United States Patent
Jackson et al.

(10) Patent No.: US 11,723,783 B2
(45) Date of Patent: Aug. 15, 2023

(54) COVERED FLOW MODIFYING APPARATUS

(71) Applicant: Neovasc Medical Ltd., Tel Aviv (IL)

(72) Inventors: Keith Alan Jackson, Brooker, FL (US); Colin Alexander Nyuli, Vancouver (CA); Shmuel Banai, Tel Aviv (IL); Fredericus Antonius Colen, Boca Raton, FL (US)

(73) Assignee: NEOVASC MEDICAL LTD., Tel Aviv (IL)

( * ) Notice: Subject to any disclaimer, the term of this patent is extended or adjusted under 35 U.S.C. 154(b) by 0 days.

(21) Appl. No.: 16/750,750

(22) Filed: Jan. 23, 2020

(65) Prior Publication Data

US 2020/0229956 A1 Jul. 23, 2020

Related U.S. Application Data

(60) Provisional application No. 62/868,356, filed on Jun. 28, 2019, provisional application No. 62/795,836, filed on Jan. 23, 2019.

(51) Int. Cl.
*A61F 2/86* (2013.01)
*A61F 2/06* (2013.01)
(Continued)

(52) U.S. Cl.
CPC .............. *A61F 2/915* (2013.01); *A61F 2/848* (2013.01); *A61F 2/86* (2013.01); *A61F 2/958* (2013.01);
(Continued)

(58) Field of Classification Search
CPC ....................................................... A61F 2/068
See application file for complete search history.

(56) References Cited

U.S. PATENT DOCUMENTS 3,334,629 A 8/1967 Cohn
3,620,218 A 11/1971 Edward et al.
(Continued)

FOREIGN PATENT DOCUMENTS

AU 2020210935 B2 8/2022
CA 2404330 A1 10/2001
(Continued)

OTHER PUBLICATIONS

Braunwald, E, "Heart Disease: A textbook of Cardiovascular Medicine", Chapter 36. pp. 1168-1169, 5th Edition, vol. 2, (1997), 5 pgs.
(Continued)

*Primary Examiner* — Leslie Lopez
(74) *Attorney, Agent, or Firm* — Morrison & Foerster LLP

(57) ABSTRACT

A flow modifying apparatus may include a plurality of struts coupled together to form a radially expandable frame having a proximal end and a distal end. The proximal and distal ends may be radially expandable into expanded proximal and distal ends. A reduced diameter portion of the expandable frame may be disposed between the expanded proximal and distal ends and the reduced diameter portion may comprise a fluid flow through passage. A cover may be disposed over at least a portion of the radially expandable frame. The reduced diameter portion modifies fluid flow therethrough immediately upon implantation thereof and forms a pressure gradient between the inflow end and the reduced diameter portion.

19 Claims, 17 Drawing Sheets

(51) Int. Cl.
*A61F 2/90* (2013.01)
*A61F 2/915* (2013.01)
*A61F 2/848* (2013.01)
*A61F 2/958* (2013.01)
*A61F 2/91* (2013.01)

(52) U.S. Cl.
CPC . *A61F 2/90* (2013.01); *A61F 2/91* (2013.01); *A61F 2002/068* (2013.01); *A61F 2002/91525* (2013.01); *A61F 2002/91533* (2013.01); *A61F 2002/91575* (2013.01); *A61F 2210/0076* (2013.01); *A61F 2230/008* (2013.01); *A61F 2230/0078* (2013.01); *A61F 2250/0018* (2013.01); *A61F 2250/0039* (2013.01)

(56) References Cited

U.S. PATENT DOCUMENTS

| | | |
|---|---|---|
| 3,739,402 A | 6/1973 | Cooley et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,292,974 A | 10/1981 | Fogarty et al. |
| 4,297,749 A | 11/1981 | Davis et al. |
| 4,339,831 A | 7/1982 | Johnson |
| 4,340,977 A | 7/1982 | Brownlee et al. |
| 4,470,157 A | 9/1984 | Love |
| 4,490,859 A | 1/1985 | Black et al. |
| 4,494,531 A | 1/1985 | Gianturco |
| 4,501,263 A | 2/1985 | Harbuck |
| 4,601,718 A | 7/1986 | Possis et al. |
| 4,705,517 A | 11/1987 | Dipisa, Jr. |
| 4,727,873 A | 3/1988 | Mobin-Uddin |
| 4,776,337 A | 10/1988 | Palmaz |
| 4,787,388 A | 11/1988 | Hofmann |
| 4,813,934 A | 3/1989 | Engelson et al. |
| 4,865,600 A | 9/1989 | Carpentier et al. |
| 4,893,623 A | 1/1990 | Rosenbluth |
| 4,994,066 A | 2/1991 | Voss |
| 5,007,926 A | 4/1991 | Derbyshire |
| 5,026,377 A | 6/1991 | Burton et al. |
| 5,064,435 A | 11/1991 | Porter |
| 5,078,736 A | 1/1992 | Behl |
| 5,123,918 A | 6/1992 | Perrier et al. |
| 5,129,902 A | 7/1992 | Goble et al. |
| 5,201,757 A | 4/1993 | Heyn et al. |
| 5,209,727 A | 5/1993 | Radisch, Jr. et al. |
| 5,211,654 A | 5/1993 | Kaltenbach |
| 5,222,980 A | 6/1993 | Gealow |
| 5,246,445 A | 9/1993 | Yachia et al. |
| 5,282,823 A | 2/1994 | Schwartz et al. |
| 5,304,194 A | 4/1994 | Chee et al. |
| 5,304,220 A | 4/1994 | Maginot |
| 5,330,482 A | 7/1994 | Gibbs et al. |
| 5,342,348 A | 8/1994 | Kaplan |
| 5,354,309 A | 10/1994 | Schnepp-Pesch et al. |
| 5,375,612 A | 12/1994 | Cottenceau et al. |
| 5,382,261 A | 1/1995 | Palmaz |
| 5,397,351 A | 3/1995 | Pavcnik et al. |
| 5,397,355 A | 3/1995 | Marin et al. |
| 5,409,019 A | 4/1995 | Wilk |
| 5,415,667 A | 5/1995 | Frater |
| 5,425,765 A | 6/1995 | Tiefenbrun et al. |
| 5,449,373 A | 9/1995 | Pinchasik et al. |
| 5,464,449 A | 11/1995 | Ryan et al. |
| 5,476,506 A | 12/1995 | Lunn |
| 5,489,297 A | 2/1996 | Duran |
| 5,500,014 A | 3/1996 | Quijano et al. |
| 5,514,176 A | 5/1996 | Bosley, Jr. |
| 5,554,152 A | 9/1996 | Aita et al. |
| 5,554,185 A | 9/1996 | Block et al. |
| 5,575,818 A | 11/1996 | Pinchuk |
| 5,609,574 A | 3/1997 | Kaplan et al. |
| 5,609,627 A | 3/1997 | Goicoechea et al. |
| 5,618,301 A | 4/1997 | Hauenstein et al. |
| 5,620,439 A | 4/1997 | Abela et al. |
| 5,622,713 A | 4/1997 | Mehlhorn |
| 5,628,788 A | 5/1997 | Pinchuk |
| 5,634,946 A | 6/1997 | Slepian |
| 5,645,551 A | 7/1997 | Green et al. |
| 5,653,743 A | 8/1997 | Martin |
| 5,653,744 A | 8/1997 | Khouri |
| 5,655,548 A | 8/1997 | Nelson et al. |
| 5,662,713 A | 9/1997 | Andersen et al. |
| 5,669,919 A | 9/1997 | Sanders et al. |
| 5,683,411 A | 11/1997 | Kavteladze et al. |
| 5,695,504 A | 12/1997 | Gifford, III et al. |
| 5,709,335 A | 1/1998 | Heck |
| 5,713,908 A | 2/1998 | Jameel et al. |
| 5,716,393 A | 2/1998 | Lindenberg et al. |
| 5,732,872 A | 3/1998 | Bolduc et al. |
| 5,741,333 A | 4/1998 | Frid |
| 5,755,769 A | 5/1998 | Richard et al. |
| 5,755,779 A | 5/1998 | Horiguchi |
| 5,772,668 A | 6/1998 | Summers et al. |
| 5,776,164 A | 7/1998 | Ripart |
| 5,782,844 A | 7/1998 | Yoon et al. |
| 5,782,905 A | 7/1998 | Richter |
| 5,797,930 A | 8/1998 | Ovil |
| 5,797,935 A | 8/1998 | Barath |
| 5,810,850 A | 9/1998 | Hathaway et al. |
| 5,840,081 A | 11/1998 | Andersen et al. |
| 5,843,117 A | 12/1998 | Alt et al. |
| 5,863,284 A | 1/1999 | Klein |
| 5,868,782 A | 2/1999 | Frantzen |
| 5,873,906 A | 2/1999 | Lau et al. |
| 5,876,418 A | 3/1999 | Karlheinzhauenstein et al. |
| 5,876,445 A | 3/1999 | Andersen et al. |
| 5,897,588 A | 4/1999 | Hull et al. |
| 5,919,224 A | 7/1999 | Thompson et al. |
| 5,922,393 A | 7/1999 | Jayaraman |
| 5,925,063 A | 7/1999 | Khosravi |
| 5,957,976 A | 9/1999 | Vanney et al. |
| 6,013,055 A | 1/2000 | Bampos et al. |
| 6,015,432 A | 1/2000 | Rakos et al. |
| 6,042,606 A | 3/2000 | Frantzen |
| 6,053,873 A | 4/2000 | Govari et al. |
| 6,063,113 A | 5/2000 | Kavteladze et al. |
| 6,070,589 A | 6/2000 | Keith et al. |
| 6,071,292 A | 6/2000 | Makower et al. |
| 6,086,612 A | 7/2000 | Jansen |
| 6,102,845 A | 8/2000 | Woodard et al. |
| 6,110,198 A | 8/2000 | Fogarty et al. |
| 6,113,631 A | 9/2000 | Jansen |
| 6,120,534 A | 9/2000 | Ruiz |
| 6,120,535 A | 9/2000 | Mcdonald et al. |
| 6,129,706 A | 10/2000 | Janacek |
| 6,159,156 A | 12/2000 | Van Bockel |
| 6,165,211 A | 12/2000 | Thompson |
| 6,168,614 B1 | 1/2001 | Andersen |
| 6,241,763 B1 | 6/2001 | Drasler et al. |
| 6,254,601 B1 | 7/2001 | Burbank et al. |
| 6,254,627 B1 | 7/2001 | Freidberg |
| 6,277,082 B1 | 8/2001 | Gambale |
| 6,293,968 B1 | 9/2001 | Taheri |
| 6,296,603 B1 | 10/2001 | Turnlund et al. |
| 6,299,637 B1 | 10/2001 | Shaolian et al. |
| 6,309,417 B1 | 10/2001 | Spence et al. |
| 6,312,465 B1 | 11/2001 | Griffin et al. |
| 6,325,813 B1 | 12/2001 | Hektner |
| 6,348,066 B1 | 2/2002 | Pinchuk et al. |
| 6,358,277 B1 | 3/2002 | Duran |
| 6,395,019 B2 | 5/2002 | Chobotov |
| 6,447,539 B1 | 9/2002 | Nelson et al. |
| 6,458,092 B1 | 10/2002 | Gambale et al. |
| 6,458,153 B1 | 10/2002 | Bailey et al. |
| 6,503,272 B2 | 1/2003 | Duerig et al. |
| 6,579,306 B1 | 6/2003 | Voelker et al. |
| 6,579,314 B1 | 6/2003 | Lombardi et al. |
| 6,602,286 B1 | 8/2003 | Strecker |
| 6,610,088 B1 | 8/2003 | Gabbay |
| 6,638,293 B1 | 10/2003 | Makower et al. |
| 6,641,610 B2 | 11/2003 | Wolf et al. |
| 6,764,505 B1 | 7/2004 | Hossainy et al. |

(56) References Cited

U.S. PATENT DOCUMENTS

| | | |
|---|---|---|
| 6,875,231 B2 | 4/2005 | Anduiza et al. |
| 6,929,660 B1 | 8/2005 | Ainsworth et al. |
| 6,953,476 B1 | 10/2005 | Shalev |
| 7,159,592 B1 | 1/2007 | Makower et al. |
| 7,186,265 B2 | 3/2007 | Sharkawy et al. |
| 7,235,097 B2 | 6/2007 | Calisse et al. |
| 7,524,330 B2 | 4/2009 | Berreklouw |
| 8,556,954 B2 | 10/2013 | Ben Muvhar et al. |
| 8,764,772 B2 | 7/2014 | Tekulve |
| 8,764,813 B2 | 7/2014 | Jantzen et al. |
| 8,858,612 B2 | 10/2014 | Ben-muvhar et al. |
| 8,911,489 B2 | 12/2014 | Ben-muvhar |
| 9,364,354 B2 | 6/2016 | Ben-Muvhar et al. |
| 9,424,961 B2 | 8/2016 | Oya et al. |
| 10,542,994 B2 | 1/2020 | Ben-Muvhar et al. |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2002/0032481 A1 | 3/2002 | Gabbay |
| 2002/0042646 A1 | 4/2002 | Wall |
| 2002/0151924 A1 | 10/2002 | Shiber |
| 2003/0069646 A1 | 4/2003 | Stinson |
| 2003/0070676 A1* | 4/2003 | Cooper ............ A61F 2/91 128/200.24 |
| 2003/0105517 A1 | 6/2003 | White et al. |
| 2003/0114913 A1 | 6/2003 | Spenser et al. |
| 2003/0163148 A1 | 8/2003 | Wang et al. |
| 2003/0176914 A1 | 9/2003 | Rabkin et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0158280 A1 | 8/2004 | Morris et al. |
| 2004/0193261 A1 | 9/2004 | Berreklouw |
| 2004/0215325 A1 | 10/2004 | Penn et al. |
| 2004/0225353 A1 | 11/2004 | James, Jr. et al. |
| 2004/0236411 A1 | 11/2004 | Sarac et al. |
| 2004/0243230 A1 | 12/2004 | Navia et al. |
| 2005/0055082 A1 | 3/2005 | Ben Muvhar et al. |
| 2005/0075727 A1 | 4/2005 | Wheatley |
| 2005/0107872 A1 | 5/2005 | Mensah et al. |
| 2005/0137686 A1 | 6/2005 | Salahieh et al. |
| 2005/0137690 A1 | 6/2005 | Salahieh et al. |
| 2005/0159811 A1 | 7/2005 | Lane |
| 2005/0171556 A1 | 8/2005 | Murphy |
| 2005/0182486 A1 | 8/2005 | Gabbay |
| 2005/0197687 A1* | 9/2005 | Molaei ............ A61L 31/088 623/1.2 |
| 2005/0267567 A1 | 12/2005 | Shalev |
| 2006/0020247 A1 | 1/2006 | Kagan et al. |
| 2006/0020327 A1 | 1/2006 | Lashinski et al. |
| 2006/0058872 A1 | 3/2006 | Salahieh et al. |
| 2006/0095115 A1 | 5/2006 | Bladillah et al. |
| 2006/0106449 A1 | 5/2006 | Ben Muvhar |
| 2006/0106450 A1 | 5/2006 | Ben Muvhar |
| 2006/0149360 A1 | 7/2006 | Schwammenthal et al. |
| 2006/0195183 A1 | 8/2006 | Navia et al. |
| 2006/0241745 A1 | 10/2006 | Solem |
| 2006/0259135 A1 | 11/2006 | Navia et al. |
| 2006/0259136 A1 | 11/2006 | Nguyen et al. |
| 2006/0293745 A1 | 12/2006 | Carpentier et al. |
| 2007/0043435 A1 | 2/2007 | Seguin et al. |
| 2007/0050021 A1 | 3/2007 | Johnson |
| 2007/0142906 A1 | 6/2007 | Figulla et al. |
| 2007/0179590 A1 | 8/2007 | Lu et al. |
| 2007/0185565 A1 | 8/2007 | Schwammenthal et al. |
| 2007/0255394 A1 | 11/2007 | Ryan |
| 2007/0293940 A1 | 12/2007 | Schaeffer et al. |
| 2008/0071361 A1 | 3/2008 | Tuval et al. |
| 2008/0082164 A1 | 4/2008 | Friedman |
| 2008/0097571 A1 | 4/2008 | Denison et al. |
| 2008/0147179 A1 | 6/2008 | Cai et al. |
| 2008/0177381 A1 | 7/2008 | Navia et al. |
| 2008/0183273 A1 | 7/2008 | Mesana et al. |
| 2008/0228254 A1 | 9/2008 | Ryan |
| 2008/0243245 A1 | 10/2008 | Thambar et al. |
| 2009/0005863 A1 | 1/2009 | Goetz et al. |
| 2009/0030499 A1 | 1/2009 | Dorn et al. |
| 2009/0082844 A1 | 3/2009 | Zacharias et al. |
| 2009/0138079 A1 | 5/2009 | Tuval et al. |
| 2009/0171456 A1 | 7/2009 | Kveen |
| 2009/0188964 A1 | 7/2009 | Orlov |
| 2009/0216314 A1 | 8/2009 | Quadri |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2010/0036479 A1 | 2/2010 | Hill et al. |
| 2010/0049306 A1 | 2/2010 | House et al. |
| 2010/0082094 A1 | 4/2010 | Quadri et al. |
| 2010/0114299 A1 | 5/2010 | Ben Muvhar et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0305685 A1 | 12/2010 | Millwee et al. |
| 2011/0004296 A1 | 1/2011 | Lutter et al. |
| 2011/0208297 A1 | 8/2011 | Tuval et al. |
| 2011/0264196 A1 | 10/2011 | Savage et al. |
| 2012/0041550 A1 | 2/2012 | Salahieh et al. |
| 2012/0101572 A1 | 4/2012 | Kovalsky et al. |
| 2012/0191125 A1 | 7/2012 | Babkes et al. |
| 2012/0271398 A1 | 10/2012 | Essinger et al. |
| 2012/0303116 A1 | 11/2012 | Gorman, III et al. |
| 2013/0053950 A1 | 2/2013 | Rowe et al. |
| 2013/0304200 A1 | 11/2013 | Mclean et al. |
| 2013/0310928 A1 | 11/2013 | Morriss et al. |
| 2014/0067041 A1 | 3/2014 | Ben-Muvhar et al. |
| 2014/0222136 A1 | 8/2014 | Geist et al. |
| 2014/0371778 A1 | 12/2014 | Rudakov et al. |
| 2015/0039020 A1 | 2/2015 | Cragg et al. |
| 2015/0088239 A1 | 3/2015 | Ben-Muvhar et al. |
| 2016/0256169 A1 | 9/2016 | Ben-muvhar et al. |
| 2017/0056175 A1* | 3/2017 | Chin ............ A61F 2/2475 |
| 2017/0333227 A1 | 11/2017 | Ben-muvhar |
| 2017/0340434 A1* | 11/2017 | Cerchiari ........ A61B 17/12195 |
| 2017/0367855 A1 | 12/2017 | Jenni |
| 2018/0014829 A1 | 1/2018 | Tal et al. |
| 2020/0178978 A1 | 6/2020 | Ben-muvhar et al. |

FOREIGN PATENT DOCUMENTS

| | | |
|---|---|---|
| CA | 2462509 A1 | 4/2003 |
| CA | 2769574 A1 | 4/2003 |
| CA | 2870392 A1 | 4/2003 |
| CA | 2981561 A1 | 4/2003 |
| CA | 2404330 C | 1/2011 |
| CA | 2769574 C | 12/2014 |
| CA | 2870392 C | 11/2017 |
| CA | 2981561 C | 8/2020 |
| CA | 3075142 C | 5/2022 |
| CN | 113891686 A | 1/2022 |
| DE | 2613575 A1 | 8/1977 |
| DE | 2613575 C2 | 11/1983 |
| DE | 3918736 A1 | 12/1990 |
| DE | 9101344 U1 | 7/1991 |
| DE | 19509464 C1 | 6/1996 |
| DE | 19541661 A1 | 5/1997 |
| DE | 102006052564 B3 | 12/2007 |
| EP | 0117940 A2 | 9/1984 |
| EP | 0355341 A1 | 2/1990 |
| EP | 0441516 A2 | 8/1991 |
| EP | 0461791 A1 | 12/1991 |
| EP | 0556850 A1 | 8/1993 |
| EP | 0587197 A1 | 3/1994 |
| EP | 0621015 A1 | 10/1994 |
| EP | 0441516 B1 | 3/1995 |
| EP | 0696446 A1 | 2/1996 |
| EP | 0779062 A1 | 6/1997 |
| EP | 1276437 A2 | 1/2003 |
| EP | 1276437 B1 | 3/2010 |
| FR | 2688688 A1 | 9/1993 |
| FR | 2743293 A1 | 7/1997 |
| GB | 1264471 A | 2/1972 |

(56) References Cited

FOREIGN PATENT DOCUMENTS

| | | |
|---|---|---|
| GB | 1315844 A | 5/1973 |
| JP | 07112028 A | 5/1995 |
| JP | 11501526 A | 2/1999 |
| JP | 2005503881 | 2/2005 |
| JP | 2022523490 A | 4/2022 |
| WO | WO-9206734 A1 | 4/1992 |
| WO | WO-9308767 A1 | 5/1993 |
| WO | WO-9322986 A1 | 11/1993 |
| WO | WO-9424961 A1 | 11/1994 |
| WO | WO-9508965 A1 | 4/1995 |
| WO | WO-9521592 A1 | 8/1995 |
| WO | WO-9526695 A2 | 10/1995 |
| WO | WO-9531155 A1 | 11/1995 |
| WO | WO-9727898 A1 | 8/1997 |
| WO | WO-9846115 A2 | 10/1998 |
| WO | WO-9934731 A1 | 7/1999 |
| WO | WO-9935975 A1 | 7/1999 |
| WO | WO-9965418 A1 | 12/1999 |
| WO | WO-0032092 A1 | 6/2000 |
| WO | WO-0172239 A2 | 10/2001 |
| WO | WO-03028522 A2 | 4/2003 |
| WO | WO-03028522 A3 | 1/2004 |
| WO | WO-2004014257 A1 | 2/2004 |
| WO | WO-2004014474 A1 | 2/2004 |
| WO | WO-2007058857 A2 | 5/2007 |
| WO | WO-2008005535 A2 | 1/2008 |
| WO | WO-2009033469 A1 | 3/2009 |
| WO | WO-2009053497 A1 | 4/2009 |
| WO | WO-2010057262 A1 | 5/2010 |
| WO | WO-2012035279 A1 | 3/2012 |
| WO | WO-2017051248 A1 | 3/2017 |
| WO | WO-2020154517 A1 | 7/2020 |

OTHER PUBLICATIONS

"International Application Serial No. PCT US2020 014816, International Search Report dated Apr. 22, 2020", 2 pgs.
"International Application Serial No. PCT US2020 014816, Written Opinion dated Apr. 22, 2020", 6 pgs.
"U.S. Appl. No. 16/708,915, Final Office Action dated Apr. 6, 2022", 8 pgs.
"U.S. Appl. No. 16/708,915, Non Final Office Action dated Oct. 26, 2021", 9 pgs.
"U.S. Appl. No. 16/708,915, Response filed Jan. 26, 2022 to Non Final Office Action dated Oct. 26, 2021", 7 pgs.
"Australian Application Serial No. 2020210935, First Examination Report dated Mar. 11, 2022", 3 pgs.
"Canadian Application Serial No. 3,075,142, Office Action dated May 10, 2021", 5 pgs.
"Canadian Application Serial No. 3,075,142, Response filed Sep. 7, 2021 to Office Action dated May 10, 2021", 14 pgs.
"CardiAQ Valve Technologies to pursue first-in-man studies of its transcatheter mitral valve system", Cardiac Interventions Today, (Jan. 12, 2010), 2 pgs.
"CoreValve USA", An advanced TAVR design, Medtronic.com, Accessed Jan. 27, 2015, (Jan. 27, 2015), 2 pgs.
"Edwards Lifesciences 2005 annual report", (Accessed Jan. 27, 2015), 24 pgs.
"Engager system. Precise Valve positioning", TAVR, (Jan. 28, 2015), 2 pgs.
"European Application Serial No. 20745970.2, Response to Communication persuantto Rules 161 and 162 filed Mar. 3, 2022", 11 pgs.
"International Application Serial No. PCT/US2020/014816, International Preliminary Report on Patentability dated Aug. 5, 2021", 9 pgs.
"The Jena Valve—the prosthesis", Jena Valve Technology, (Jan. 28, 2015), 1 pg.
Al-Attar, "Next generation surgical aortic biological prostheses: sutureless valves", European Society of Cardiology, (Dec. 21, 2011), 3 pgs.

Banai, et al., "Tiara: a novel catheter-based mitral valve bioprosthesis: initial experiments and short-term pre-clinical results", J Am Coll Cardiol, 60(15), (2012), 1430-1.
Beck, C S, et al., "Operations for Coronary Artery Disease", J.A.M.A.; vol. 156, No. 13, (1954), 14 pages.
Beck, C S, et al., "The surgical management of coronary artery disease: background, rationale, clinical experiences", American College of Physicians in Annals of Internal Medicine, Ann Intern Med. 45(6), (Dec. 1956), 14 pages.
Beck, C. S, et al., "Scientific basis for the surgical treatment of coronary artery disease", J Am Med Assoc., 159(13), (Nov. 26, 1955), 1264-1271.
Beck, C. S, et al., "Some new concepts of coronary heart disease; results after surgical operation", J Am Med Assoc., 168(16), (Dec. 20, 1958), 2110-2117.
Beck, C. S, et al., "The coronary patient wants better treatment", Medical Times; NY; vol. 89; No. 1, (Jan. 1961), 11 pgs.
Berreklouw, et al., "Sutureless mitral valve replacement with bioprostheses and Nitinol attachment rings: feasibility in acute pig experiments", J Thorac Cardiovasc Surg, (Feb. 4, 2011), 390-5.
Boudjemline, et al., "Steps toward the percutaneous replacement of atrioventricular valves an experimental study", J Am Coll Cardiol, (2005), 360-5.
Brinkman, "Transcatheter cardiac valve interventions", Surg Clin North Am, (2009), 951-66.
Brofman, B. L., "Long term influence of the Beck operation for coronary heart disease", American Journal of Cardiology, 6, (Aug. 1960), 259-271.
Chiam, et al., "Percutaneous transcatheter aortic valve implantation: assessing results judging outcomes, and planning trials: the interventionalist perspective", JACC Cardiovasc Interv, (2008), 341-50.
Condado, et al., "Percutaneous treatment of heart valves", Rev Esp Cardiol, (2006), 1225-31.
De Backer, et al., "Percutaneous transcatheter mitral valve replacement: an overview of devices in preclinical and early clinical evaluation", Circ Cardiovasc Interv, (Jun. 2014), 400-9 pgs.
Fanning, et al., "Transcatheter aortic valve implantation (TAVI): valve design and evolution", Int J Cardiol, (Oct. 3, 2013), 1822-31.
Faxon, M. D, et al., "Coronary sinus occlusion pressure and its relation to intracardiac pressure", The American Journal of Cardiology, vol. 58, (1985), 457-460.
Gillespie, et al., "Sutureless mitral valve replacement: initial steps toward a percutaneous procedure", Ann Thorac Surg 96(2), (2013), 4 pgs.
Gross, L., et al., "Experimental attempts to increase the blood supply to the dog's heart by means of coronary sinus occlusion", Journal Exper. Med. 65, (Jan. 1937), 20 pages.
Grube, et al., "Percutaneous implantation of the Core Valve self-expanding valve prosthesis in high-risk patients with aortic valve disease: the Siegburg first-in-man study", Circulation, (Oct. 2, 2006), 1616-24.
Harmon, et al., "Effect of acute myocardial infarction on the angle between the mitral and aortic valve plane", Am J Cardiol, 84(3), (Aug. 1999), 342-4.
Herrman, "Trancatheter mitral valve implantation", Cardiac Interventions Today, (Aug./Sep. 2009), 82-85.
Hummel, John, et al., "A Quantitative Fluoroscopic Comparison of the Coronary Sinus Ostium in Patients with and without AV Nodal Reentrant Tachycardia", J. Cardiovasc Electrophysio, vol. 6, (Sep. 1995), 681-686.
Ionasec, "Personalized modeling and assessment of the aortic-mitral coupling from 4D TEE and CT", Med Image Comput Comput Assist Interv, (2009), 767-75 pgs.
Karimi, et al., "Percutaneous Valve Therapies", Chapter 11, (2007), 11 pgs.
Kumar, et al., "Design considerations and quantitative assessment for the development of percutaneous mitral valve stent", Med Eng Phys, (Apr. 16, 2014), 882-8.
Lauten, et al., "Experimental evaluation of the JenaClip transcatheter aortic valve", Catheter Cardiovasc Interv, 74(3), (Sep. 1, 2009), 514-19.

(56) References Cited

OTHER PUBLICATIONS

Leon, et al., "Transcatheter aortic valve replacement in patients with critical aortic stenosis: rationale, device descriptions, early clinical experiences, and perspectives", Semin Thorac Cardiovasc Surg, 18(2), (2006), 165-74.
Lozonschi, et al., "Transapical mitral valved stent implantation", Ann Thorac Surg, 86(3), (2008), 745-8.
Lutter, et al., "Off-pump transapical mitral valve replacement", Eur J Cardiothorac Surg, (2009), 124-8.
Lutter, et al., "Transapical mitral valve implantation: the Lutter valve", Heart Lung Vessel, (2013), 6 pgs.
Ma, et al., "Double-crowned valved stents for off-pump mitral valve replacement", Eur J Cardiothorac Surg, (Aug. 2005), 194-8.
Maisano, "Mitral transcatheter technologies", Rambam Maimonides Med J, 4(3), (Jul. 25, 2013), 12 pgs.
Navia, et al., "Sutureless implantation a expandable mitral stent-valve prosthesis in acute animal model", TCT728. JACC vol. 58, No. 20, (Nov. 8, 2011), 1 pg.
Orton, "Mitralseal: hybrid trancatheter mitral valve replacement", Colorado State University, [Online] Retrieved from the internet: <https://www.acvs.org/files/proceedings/2011/data/papers/102.pdf.>, (2011), 311-312.
Piazza, et al., "Anatomy of the aortic valvar complex and its implications for transcatheter implantation of the aortic valve", Circ Cardiovasc Interv, (Aug. 2008), 74-81.
Pluth, et al., "Aortic and mitral valve replacement with cloth-covered Braunwald-Cutter prosthesis", A three-year follow-up. Ann Thorac Surg, (Sep. 1975), 239-48.
Preston-Maher, et al., "A Technical Review of Minimally Invasive Mitral Valve Replacements", Cardiovasc Eng Technol, (Nov. 25, 2014), 11 pgs.
Quadri, et al., "CVT is developing a non-surgical apporach to replacing mitral valves that may be the alternative to open-chest surgery", CardiAQ Valve Technologies, (May 8, 2009), 1 pg.
Ribiero, "Balloon-expandable prostheses for transcatheter aortic valve replacement", Prog Cardiovasc Dis, (Mar. 1, 2014), 583-95.
Robertson, H F, "The Reestablishment of Cardiac Circulation during Progressive Coronary Occlusion", The American Heart Journal; vol. 10, (1935), 533-541.
Sandler, G., et al., "The Beck operation in the treatment of angina pectoris", Thorax; vol. 32; No. 34, (Jan. 1967), 34-37.
Seidel, et al., "A mitral valve prosthesis and a study of thrombosis on heart valves in dogs", J Surg Res, (May 1962), 168-75.
Shuto, et al., "Percutaneous transvenous Melody valve-in-ring procedure for mitral valve replacement", J Am Coll Cardiol, (Dec. 2011), 2475-80.
Sondergaard, et al., "First-in-human CardiAQ transcatheter mitral valve implantation via transapical approach", TCT-811. JACC vol. 64, No. 11 Suppl B, (Sep. 13, 2014), 1 pg.
Spencer, et al., "Surgical treatment of valvular heart disease", Part V. Prosthetic replacement of the mitral valve. American Heart Journal, (Oct. 1968), 576-580.
Spillner, et al., "New sutureless 'atrial mitral-valve prosthesis' for minimally invasive mitral valve therapy", Textile Research Journal, (2010), 7 pgs.
Timek, et al., "Aorto-mitral annular dynamics", Ann Thorac Surg, (Dec. 2003), 1944-50.
Tsang, et al., "Changes in aortic-mitral coupling with severe aortic stenosis", JACC vol. 55. Issue 1A, (Mar. 9, 2010), 1 pg.
Veronesi, "A study of functional anatomy of aortic-mitral valve coupling using 3D matrix transesophageal echocardiography", Circ Cardiovasc Imaging, (Dec. 2, 2008), 24-31 pgs.
Vu, et al., "Novel sutureless mitral valve implantation method involving a bayonet insertion and release mechanism: A proof of concept study in pigs", J Thorac Cardiovasc Surg, (2012), 985-8.
Walther, Thomas, et al., "Transapical approach for sutureless stent-fixed aortic valve implantation: experimental results", European Journal of Cardio-thoracic Surgery, 29, (2006), 703-708.
Webb, J. G, et al., "Transcatheter aortic valve implantation: The evolution of prostheses, delivery systems and approaches", Archives of Cardiovascular Disease, 105(3), (2012), 153-159.
Wising, P. J, "The Beck-I operation for angina pectoris", Acta Medica Scandinavica, 174; Fasc. 1, (Jul. 1963), 93-98.
Zalewski, A, et al., "Myocardial protection via coronary sinus interventions: superior effects of arterialization compared with intermittent occlusion", Laboratory Investigation—Myocardial Ischemia; vol. 71; No. 6, (Jun. 1985), 1215-1223.
"Australian Application Serial No. 2020210935, Response filed Jun. 29, 2022 to First Examination Report dated Mar. 11, 2022", 16 pgs.
"Canadian Application Serial No. 3,127,324, Office Action dated Oct. 17, 2022", 5 pgs.
"European Application Serial No. 20745970.2, Extended European Search Report dated Sep. 27, 2022", 8 pgs.
"Japanese Application Serial No. 2021-543301, Notification of Reasons for Refusal dated Nov. 28, 2022", w English Translation, 10 pgs.
"Japanese Application Serial No. 2021-543301, Response filed Feb. 14, 2023 to Notification of Reasons for Refusal dated Nov. 28, 2022", w English Claims, 11 pgs.
"Canadian Application Serial No. 3,127,324, Response filed Feb. 15, 2023 to Office Action dated Oct. 17, 2022", 23 pgs.

\* cited by examiner

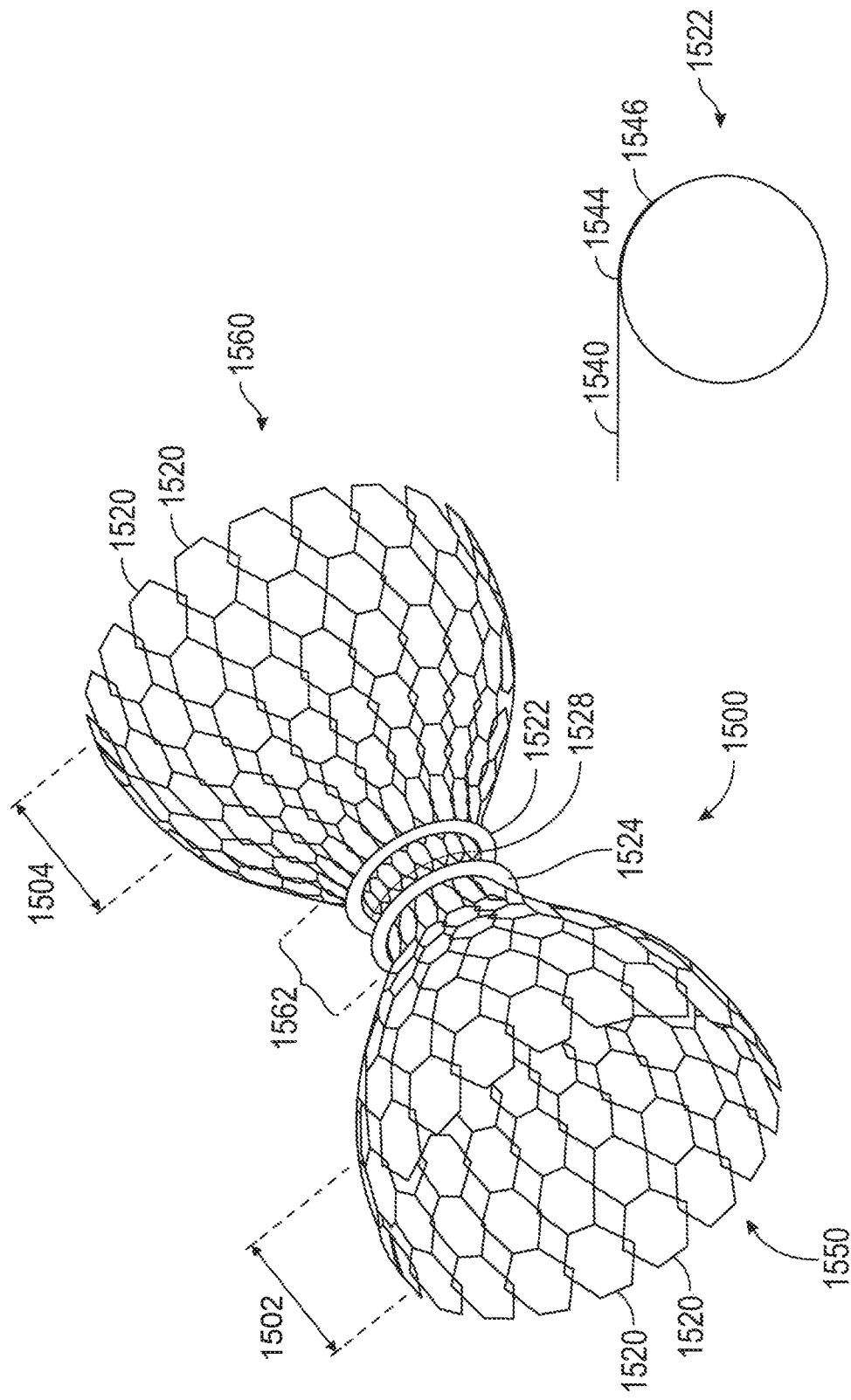

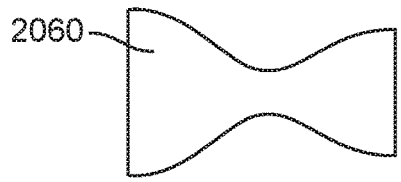
FIG. 11A1
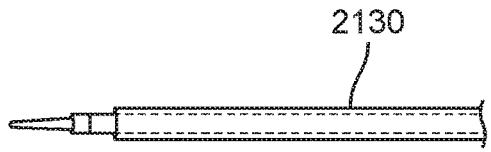
FIG. 11B1
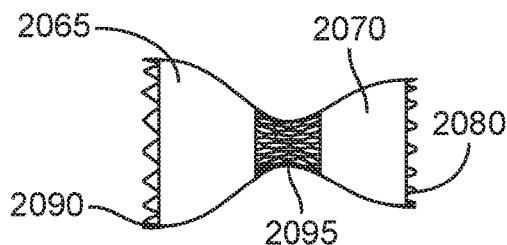
FIG. 11A2
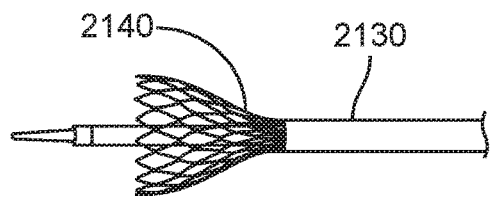
FIG. 11B2
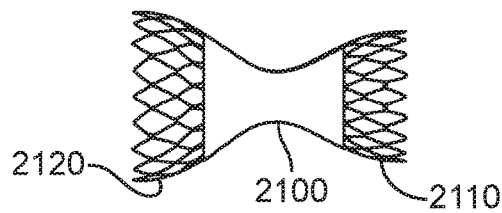
FIG. 11A3
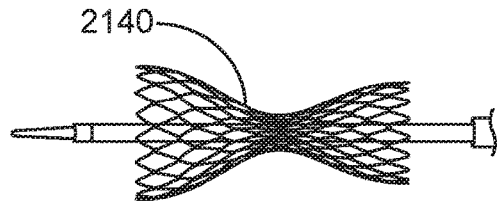
FIG. 11B3
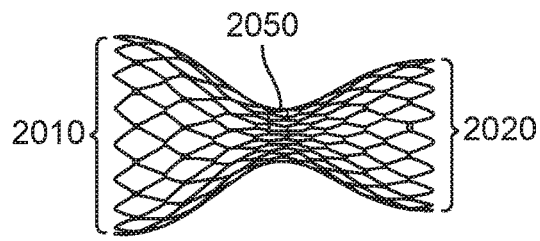
FIG. 11C
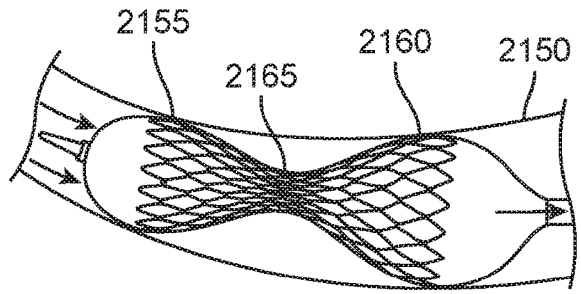
FIG. 11D

COVERED FLOW MODIFYING APPARATUS

CLAIM OF PRIORITY

This patent application claims the benefit of priority of U.S. Provisional Patent Application Ser. No. 62/795,836 filed on Jan. 23, 2019, and U.S. Provisional Patent Application Ser. No. 62/868,356 filed on Jun. 28, 2019; each of which is hereby incorporated by reference herein in its entirety

CROSS-REFERENCE TO RELATED PATENT DOCUMENTS

The present application is related to U.S. Pat. No. 9,364,354; the entire contents of which are incorporated herein by reference.

BACKGROUND

Occlusion and/or narrowing of coronary arteries can result in chronic pain known as angina. While not life threatening, angina can result in a modified quality of life. Various treatments exist to address angina such as medications, stent implantation, balloon angioplasty, coronary artery bypass grafting (CABG). Angina pectoris, refractory to medical and interventional therapies, is a common and disabling medical condition, and a major public health problem that affects millions of patients worldwide. It is common not only in patients who are not good candidates for revascularization, but also in patients following successful revascularization. The prevalence of angina is as high as 25% after 1 year, and up to 45% after 3 years following revascularization. Various treatments for angina are currently available. Each treatment is promising but may be limited to certain indications for use and thus new treatments are desirable.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIGS. 8A-8B are an isometric view and detail, respectively, of a ringed mesh-type flow modifying implant.

FIGS. 11A1-11A3 illustrate examples of flow modifying implants.

FIGS. 11B1-11B3 illustrate a delivery system and delivery sequence for a flow modifying apparatus.

FIG. 11C illustrates an example of a flow modifying implant.

FIG. 11D illustrates a flow modifying implant deployed in a blood vessel.

DETAILED DESCRIPTION

Figure 1:
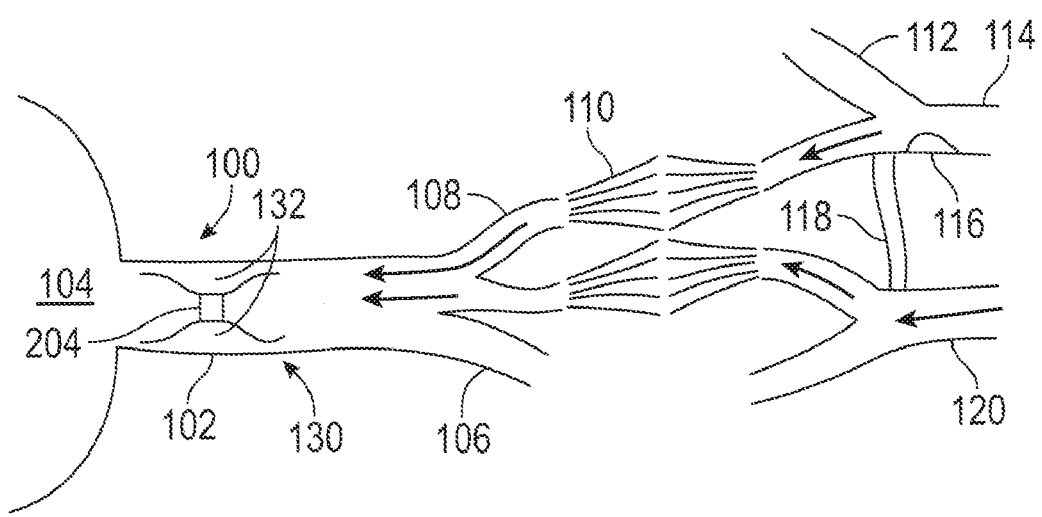
FIG. 1 is a schematic showing a flow modifying implant implanted in a coronary sinus vein.

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 1 is a schematic showing a flow modifying implant 100 installed in a coronary sinus vein 102. Coronary sinus 102 drains a plurality of cardiac veins 106 into a right atrium 104. The cardiac circulation is generally hierarchical and comprises stages of reducing (or increasing) diameter vessels. Thus, veins 106, in turn, drain a plurality of thin venules 108, which, after a few stages, drain a plurality of capillaries 110. Capillaries 110 are fed by a plurality of arterioles 112, which, after a few stages, are fed by a plurality of coronary arteries 114 and 120. A stenosis 116 is shown in a coronary artery 114. While the cardiac circulation is generally hierarchical, some connection exists between different branches. Occasionally, the existence of stenosis 116 will cause a collateral connection 118 to spontaneously form (or widen an existing connection) between coronaries 114 and 120, bypassing stenosis 116.

In some cases, however, this spontaneous formation does not occur. In any example, a flow modifying implant 100 is placed in coronary sinus 102 and has a narrowing significant enough to encourage the formation of collateral connection 118. Without being bound by any theory it is hypothesized that collateral connection 118 is caused by an increase in venous blood pressure, which, in turn, increases the pressure in the capillaries and/or causes retrograde flow in the capillaries and/or causes drainage of the capillaries directly into the heart. However, even if this hypothesis is incorrect, several studies that included numerous experiments and actual procedures have shown that constriction of the coronary sinus 102 will generally cause the formation of collateral circulation and/or otherwise improve the condition of patients with blocked coronary arteries. Alternative or additional hypotheses that are optionally used to select the constrictive effect of flow modifying implant 100 include:

(a) Flow modifying implant 100 increases the pressure upstream of the implant in the coronary capillaries, thus increasing perfusion duration.

(b) An increase in resistance of the venous system causes redistribution of blood flow in coronary arteries.

(c) An increase in resistance of venous system increases intra-myocardial perfusion pressure and/or intra-myocardial pressure.

(d) Increasing the arterial diastolic pressure (by restricting venous drainage) causes the arterial auto-regulation to start working again, for example, such an auto regulation as described in Braunwald "Heart Disease: A Textbook of Cardiovascular Medicine, 5th Edition, 1997, W. B. Saunders Company, Chapter 36, pages 1168-1169.

It should be noted that the selection of flow modifying implant 100 may be made to achieve one or more of the above suggested effects, optionally to a desired degree and/or accounting for safety issues, such as allowing some drainage and maximum pressure allowed by the coronary venous drainage system.

Figure 2:
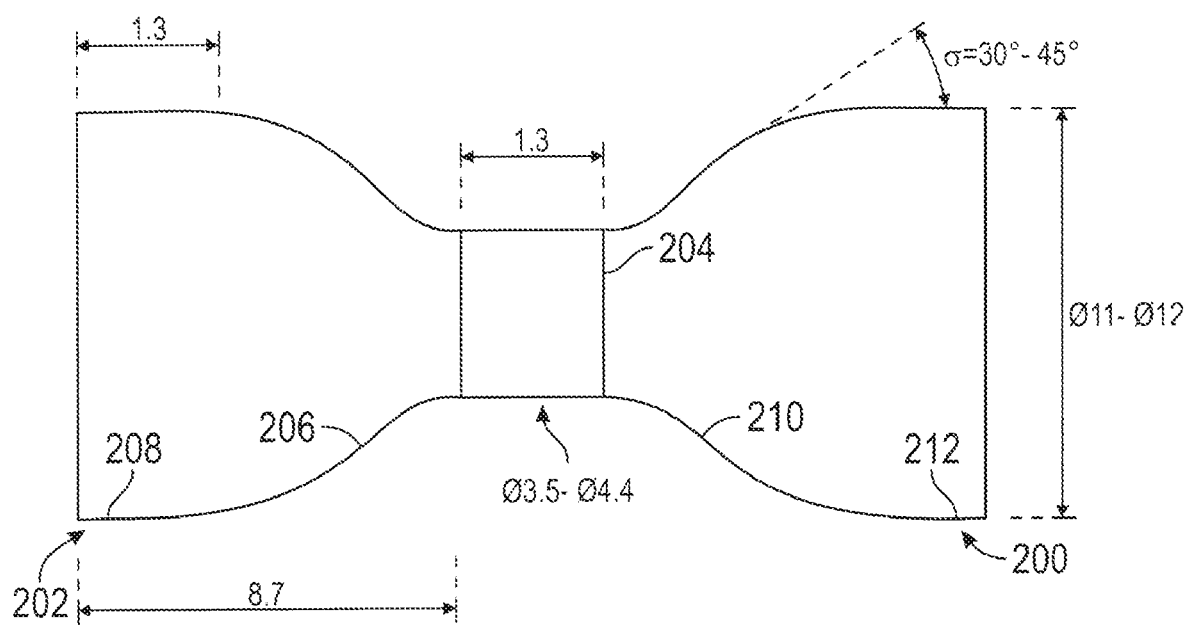
FIG. 2 is a schematic side view of a flow modifying implant.

FIG. 2 is a schematic side view of flow modifying implant 100, which may be used in any example herein. Flow modifying implant 100 comprises a narrowed section 204 and at least one flared section 200 (and optionally the opposite end 202 is also flared) leading into narrowed section 204. Section 200 (and optionally 202) includes sections 210 and 206 that are inclined relative to the wall of coronary sinus 102 and sections 212 and 208 that are substantially parallel to the vessel wall.

In the example and measurements shown or any example herein, flow modifying implant 100 is radially expandable and may foreshorten somewhat during expansion: the implant may have a length of 20 mm before expansion and about 18.8 mm after expansion. Optionally in any example, a non-shortening design may be is used, for example a mesh as in peristaltic stents, such as described in U.S. Pat. No. 5,662,713, the disclosure of which is incorporated herein by reference. An example of material thickness that may be used is 0.15 mm, however, thinner or thicker materials may be used. Other examples of implant lengths are 5 mm, 12 mm, 24 mm, 35 mm 45 mm and any smaller, intermediate or larger size may be used. The length is optionally selected to match a physiological size of the target vein (e.g., length and curves) and/or to ensure good contact with vein walls. The length of narrowed section 204 may be, for example, 0.5 mm, 1 mm, 2 mm, 3 mm, 5 mm or any smaller, intermediate or larger length may be used to achieve desired flow dynamics. An example inner diameter of the flared sections is between 2 mm and 30 mm, for example, 5 mm, 10 mm, 15 mm, 20 mm or any larger, smaller or intermediate diameter may be used in any example, to match the vein or vessel diameter. The inner diameter of the narrowed section may be, for example, 1 mm, 2 mm, 3 mm, 5 mm, 10 mm or any smaller, larger or intermediate diameter may be used in any example to achieve desired flow dynamics and/or a desired pressure differential across the flow modifying implant.

In any example of a flow modifying implant, the ratio between the cross-section of narrowed section 204 and the flares of flow modifying implant 100 may be 0.9, 0.8, 0.6, 0.4, 0.2 or any larger, smaller or intermediate ratio may be used to achieve desired flow dynamics and/or a desired pressure differential across the flow modifying implant.

While a circular cross-section is shown, any other cross-section may be used, for example, polygonal, oval, and ellipsoid. A potential advantage of non-circular cross-sections is that the implant is less likely to migrate axially and/or rotate. Alternatively, or additionally in any example, the outside of the flow modifying implant is roughened and/or otherwise adapted to adhere to the vein wall. The cross-section shape and/or orientation in any example may optionally change along the length of flow modifying implant 100.

Figure 3A:
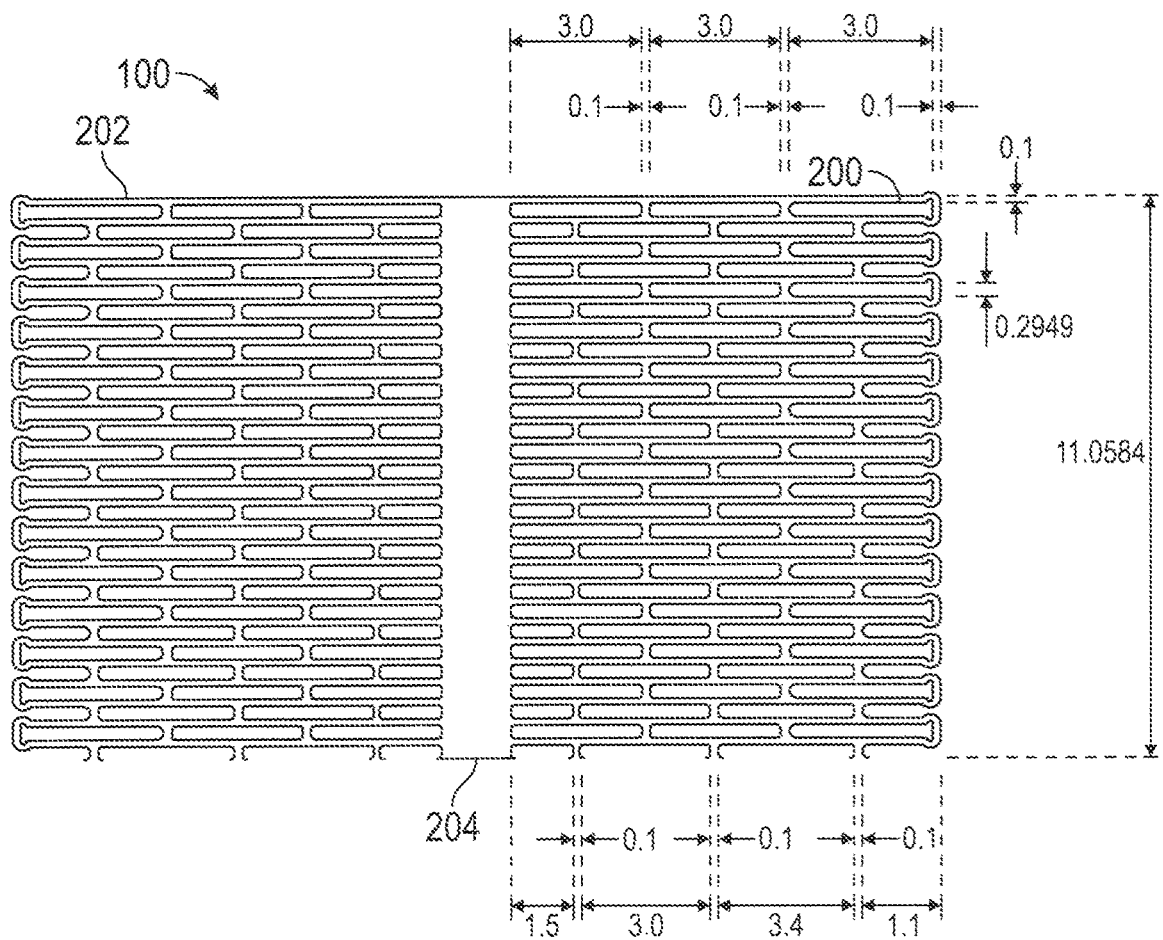
FIGS. 3A-3B illustrate an example of a flow modifying implant.
Figure 3B:
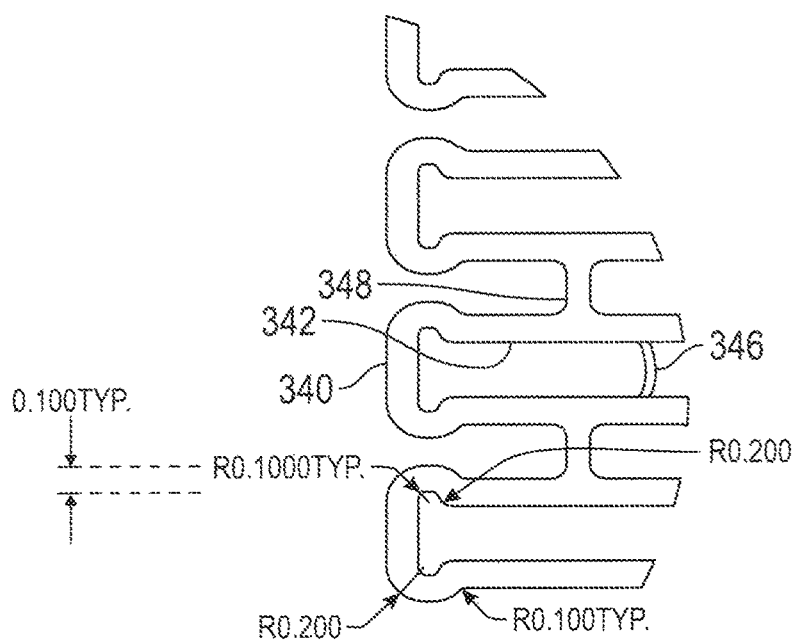

FIG. 3A is a flat layout of a cut pattern of a slit-type flow modifying implant and FIG. 3B is a detail of FIG. 3A. In this plan layout, the ends of sections 200 and 202 are caused to be parallel to the vessel wall when flow modifying implant 100 is expanded.

In any example, the outside flare of flow modifying implant 100 is defined by sections 340 and 342, shown in FIG. 3B. Optionally, in any example the total length of these sections defines the maximum flare length. Alternatively, or additionally in any example, the bending areas in and between these sections define the relative force required to expand the flare region relative to the area near the rim. If the rim region is more difficult to expand and/or is expanded less than the adjacent regions, the expansion of flow modifying implant 100 will tend to cause the rim to be bent in, or at least not flare out. Alternatively, in a self-expanding flow modifying implant, the existence of sections 340 and 342 can be used to determine the final shape of the flare. Optionally in any example, additional sections 346 are provided around the circumference of flow modifying implant 100, which define outer slits in flow modifying implant 100, which outer slits may have a maximum expansion that is the same or smaller than nearby (axially inwards) slits. This design can also be used to control the shape of the flare.

The implant may be cut from hypodermic needle tubing with a laser or by electrical discharge machining so as to have a plurality of elongate axial oriented slots that are substantially parallel to the longitudinal axis of the device. Each slot is defined by a plurality of struts which are axially oriented struts and are connected together with a circumferentially oriented connector element thereby forming a series of rectangular slots in the collapsed configuration. The slots may exist on either side of the flat layout of the cut pattern 100, and an intermediate portion 204 with or without slots. The opposite ends of the device may have smooth edges formed from a connector element that joins the elongate struts. The connector element may have an arcuate region forming an enlarged head region at the end. When a radial force such as from a balloon is applied to the inner diameter of the device, the device expands radially outward into an expanded configuration forming the flares.

In any example of the flow modifying implant, the implant may be characterized by this maximum diameter, which may be used, for example, for selecting a particular flow modifying implant to match a patient. Optionally in any example of the implant, during expansion, the balloon is aligned with flow modifying implant 100 so that it only contacts the flare region or only contacts the non-flare regions of flow modifying implant 100.

Figure 3C:
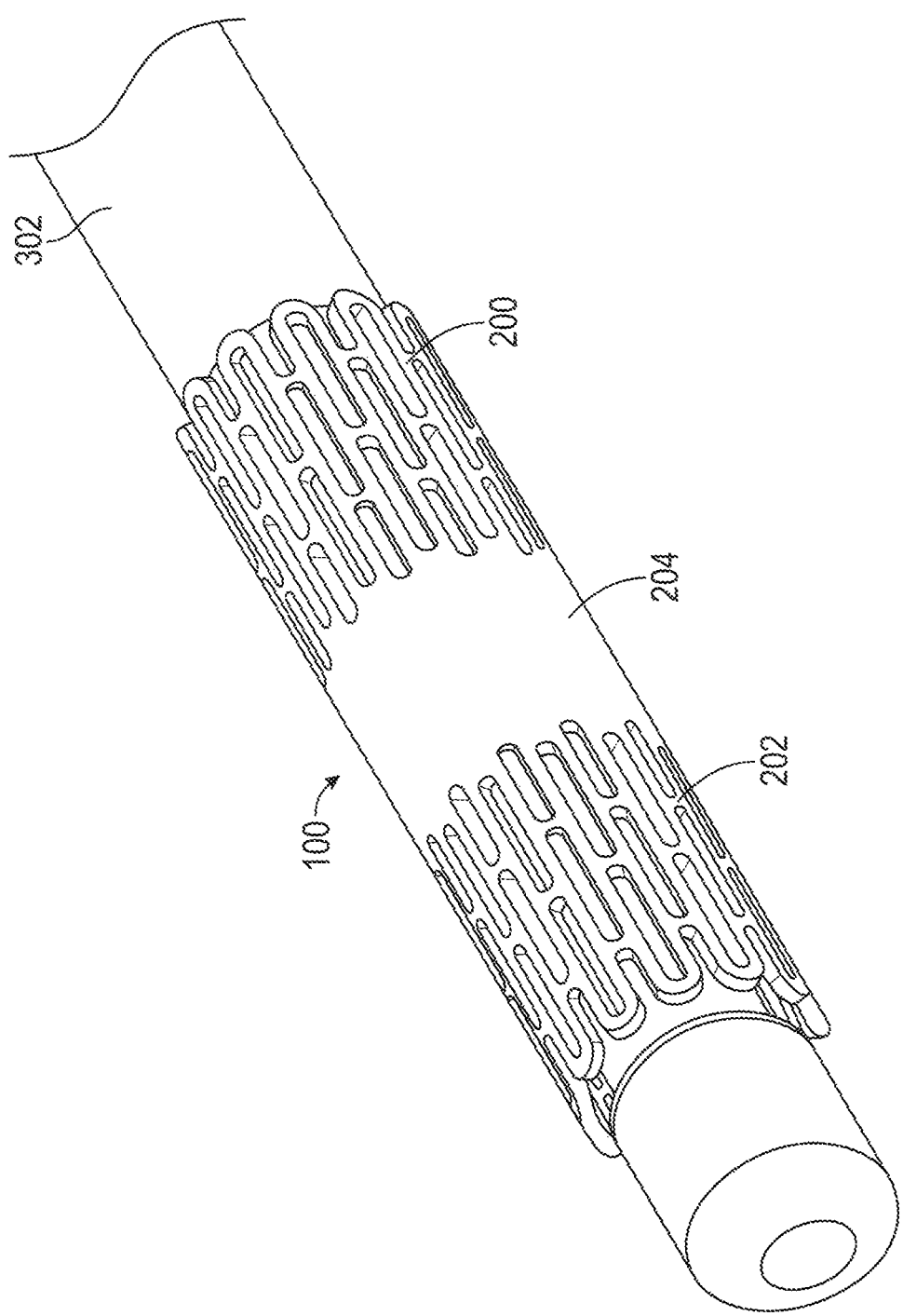
FIG. 3C is an isometric view of the flow modifying implant of FIG. 3A mounted on a delivery catheter.

FIG. 3C is an isometric view of flow modifying implant 100 (FIG. 3A), mounted on a balloon catheter delivery system 302, in accordance with an example of the invention.

In any example of the implant, flow modifying implant 100 is formed by cutting out of a sheet of metal or a tube, for example, using laser, water cutting, chemical erosion or metal stamping (e.g., with the result being welded to form a tube). Alternatively, flow modifying implant 100 is woven (e.g. of metal or plastic fiber), for example, using methods as well known in the art. Optionally in any example, narrowed section 204 is made using a different method from flared sections 200 and 202, for example, the flared sections being woven, and the narrowed section being cut from sheet metal. In any example, the flow modifying implant may include a constraining ring that prevents the expansion of narrowed section 204. Optionally in any example, the restraining ring is plastically expandable, possibly under a higher pressure than the rest of flow modifying implant 100, which may be plastically deformable or self-expanding. Alternatively, or additionally in any example, the restraining ring is selected to set the desired degree of narrowing, and then mounted on a flow modifying implant, a stent or a stent graft, for implantation. In a sleeve flow modifying implant (FIG. 7G) a similar effect may be achieved by suturing the stent graft.

Upon delivering of the implant to a target treatment site, a standard balloon catheter with a single expansion area, for example the Fox Catheter™ by Jomed, Inc., may be used to encourage the implant to attain its contoured shape. As the balloon presses against lumen of the implant, the narrowed section is prevented from expanding while flared sections 200 and 202 expand under pressure. Various methods for preventing the narrow section from expanding are described below, for example, providing different mechanical properties, different designs or additional elements at the narrowed sections relative to the non-narrowed sections.

In any example of the implant, flow modifying implant 100 may be cut out of a sheet and then spirally twisted around a mandrel to form the shape of flow modifying implant 100. Alternatively, flow modifying implant 100 is cut out of a tube, with the flared parts being spiral cuts and the narrowing part being a ring cut. Alternatively, flow modifying implant 100 is formed as a coil spring, with axially varying relaxation positions.

In any example of the implant, flow modifying implant 100 may be adapted for use in a coronary sinus or other coronary vein or other veins having non-muscular walls. Veins are typified by having a low degree of elasticity and being relatively sensitive to tears (as compared to arteries). In any example, the edges of flow modifying implant 100 are curved inwards or curled, for example as shown by reference 130 in FIG. 1. Alternatively, or additionally in any example in any example, the edges are folded back and/or smoothed to remove sharp edges. Alternatively, the parallel sections 208 and 212 (FIG. 2) are made long enough to support flow modifying implant 100 without harming coronary sinus 102. Alternatively, or additionally in any example, flow modifying implant 100 or at least a larger diameter portion thereof, is made soft enough and/or with a low spring constant, to prevent flow modifying implant 100 from applying too much pressure on the coronary flow modifying implant wall. Alternatively, or additionally in any example, the flares of flow modifying implant 100 are coated with a biologically inert flexible coating, for example, a soft silicone elastomer or another soft plastic or rubber material such as Latex, Teflon and/or polyurethane (for example Angioflex, a biologically inert polyurethane plastic).

Figure 4A:
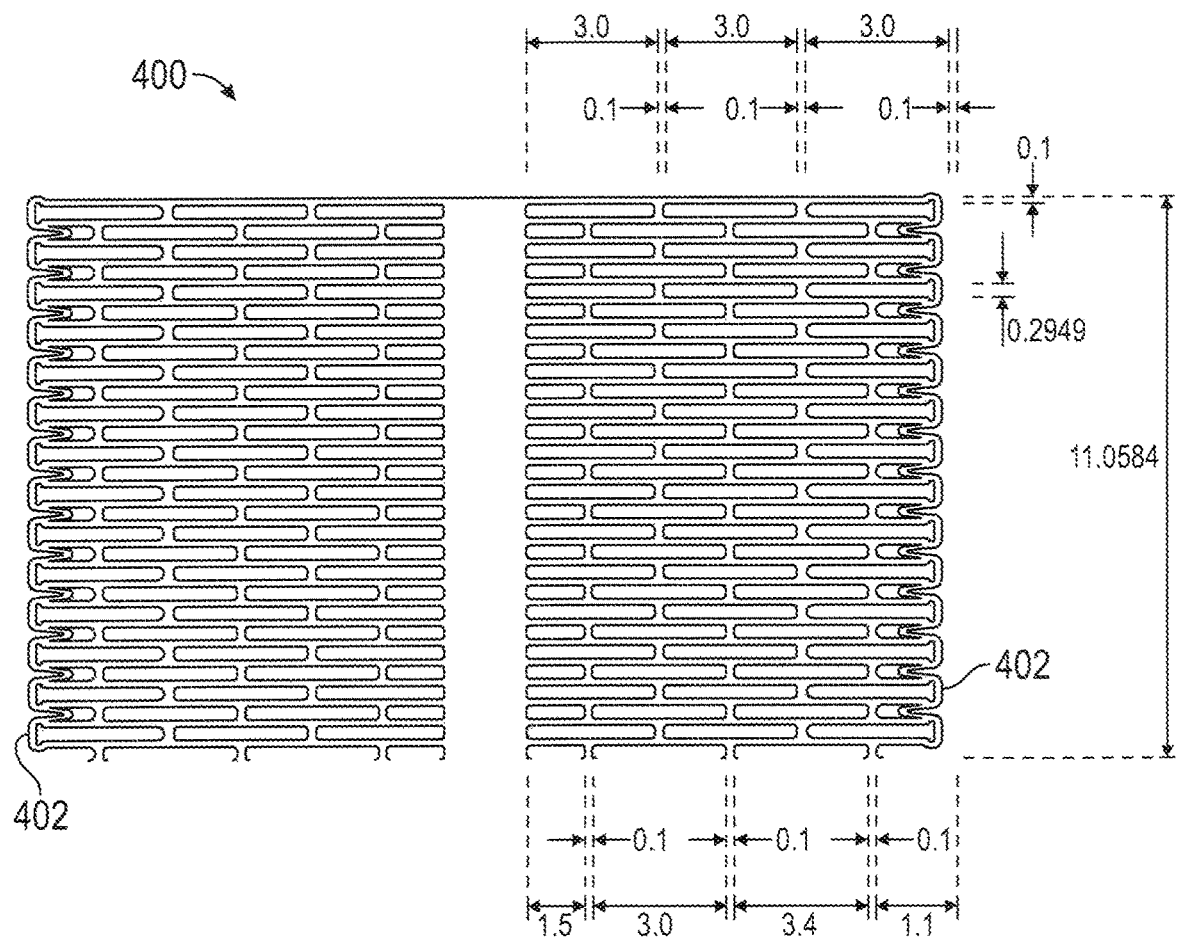
FIGS. 4A-4B illustrate plan layouts of a slit-type flow modifying implant.
Figure 4B:
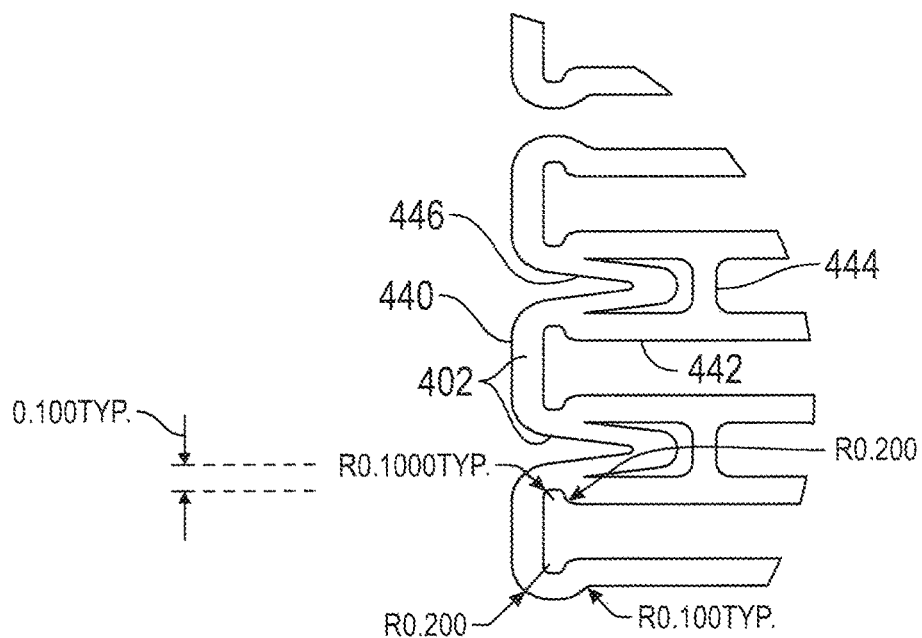

FIGS. 4A-4B are plan layouts of slit-type flow modifying implant 100. In FIG. 4B, rim 402 is defined by sections 440 and 446. As shown, these sections are designed to provide a relatively smooth rim, possibly with small amounts of distortion (so rim 402 remains smooth) where the sections connect to sections 442 and 444. Together, sections 442, 444 and 446 define outer slits for rim 402. The structure of the implant such as the struts, slots, and connector elements generally take the same form as previously described in FIG. 3A-3C. Optionally or additionally, in any example, there may be a connector 446 which may be in a "V" shape in a collapsed configuration. When expanded, the "V" shape may become a linear and circumferentially oriented strut that defines the rim as best seen in FIG. 4C.

Patients that are candidates for an angiogenesis-promoting procedure may have significant vascular compromise of the coronary circulation with constriction and/or lack of flow in one or more coronary arteries that supply blood to the coronary tissue. An invasive surgical procedure, even to percutaneously introduce and/or position a reducing implant 100 into the coronary sinus, may trigger a cardiovascular accident with untoward sequella. Hence, averting and/or limiting the amount of time that the vasculature is invaded, for example, during use of a balloon catheter is desirable in some individuals.

Figure 4C:
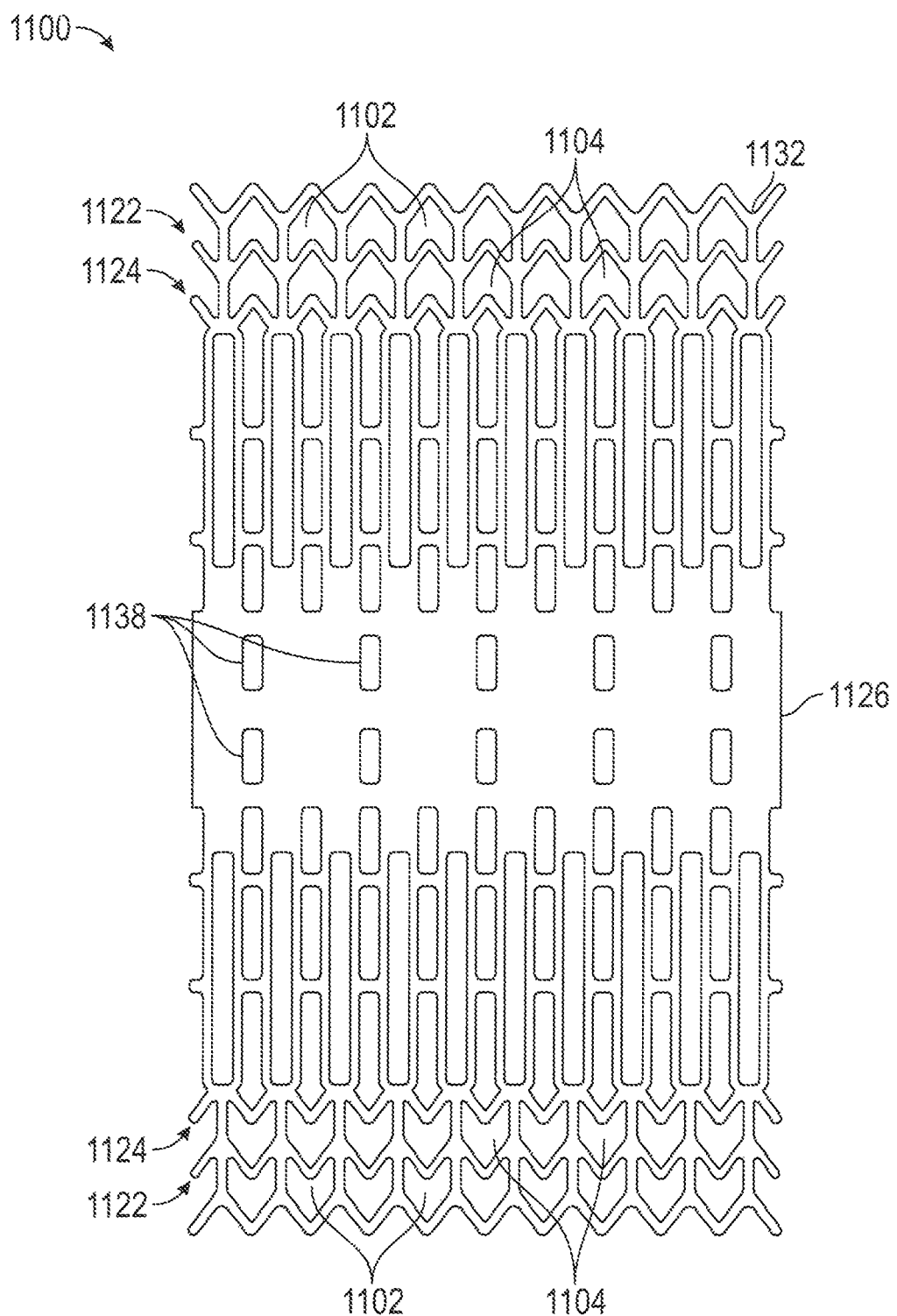
FIGS. 4C-4D are a plan layout and isometric view, respectively, of a slit-type flow modifying implant with a smooth rim.
Figure 4D:
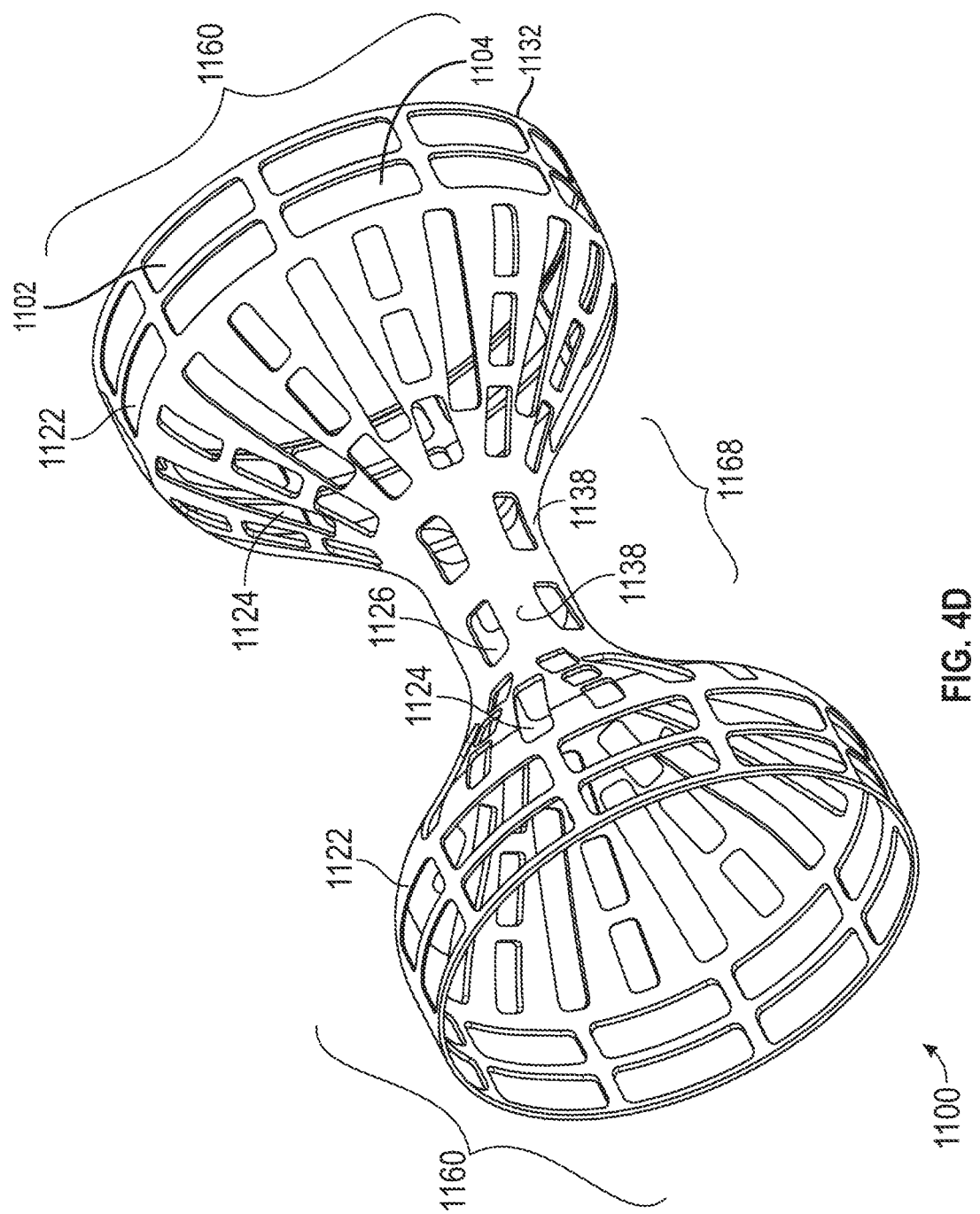

FIGS. 4C-4D are a plan layout and isometric view, respectively of a slit-type flow modifying implant 1100 with a smooth rim.

In any example, slit-type flow-modifying implant 1100 comprises shape memory materials (e.g. Nitinol) that automatically achieve a final configuration state upon exiting, for example, a delivery catheter or sheath, thereby averting the use of a balloon catheter for initial deployment and implantation of slit-type flow-modifying implant 1100. Alternatively, a balloon expandable material, for example one that plastically deforms by expansion, may be used.

In any example, slit-type coronary flow-modifying implant 1100, shown in a plan view in FIG. 4C, contains preformed slits 1102. Slits 1102 (and optionally a set of slits 1104 in a second or further row) define a row 1122 (and a row 1124) along an outer edge 1132 of slit-type flow modifying implant 1100 that, in the unexpanded state comprise at least one edge 1132 that has a scalloped configuration. Upon expansion, for example shown in FIG. 4D, edge 1132 becomes smooth and linear while slits 1102 assume a rectangular appearance, with edge 1132 transverse to a slit 1126, for example. In any example of the invention, the slits of the rim are wider than the slits of the rest of implant 1100, thereby affecting its final expanded configuration.

In any example, slit-type coronary flow-modifying implant 1100 is transferred to its deployment site in the coronary sinus using a guide sheath without accompaniment by a balloon catheter. As slit-type coronary flow-modifying implant 1100 reaches its destination and exits its guide sheath, coronary flow-modifying implant 1100 automatically expands into its final shape, shown in FIG. 4D. In this manner, slit-type coronary flow-modifying implant 1100 does not require manipulation and/or expansion using, for example, a balloon catheter.

Alternatively, or additionally in any example, a balloon catheter may be used to facilitate expansion of slit-type flow-modifying implant 1100, for example, when it is made of materials that do not automatically attain a memorized shape. In any example, rows of slits 1122 and/or 1124 have lengths and/or orientations that promote flow-modifying implant 1100 to form into a final shape under pressure of a balloon catheter, therefore, installing with a minimal amount of time and/or stress to the surrounding tissue.

In any example, the implant may have an hourglass shaped body where there are enlarged opposite ends and a constricted intermediate section. The enlarged ends may include a flared section and a rim section. The flared section may be a monotonically increasing flared section and a constant diameter rim section. The intermediate section may be substantially cylindrical. In the flared section, there are a plurality of elongate axially oriented slots which are generally parallel to the longitudinal axis of the device. Each slot is surrounded by several struts including a plurality of axially oriented struts, substantially parallel to the longitudinal axis and connected together with one or more circumferentially oriented connector elements thereby defining a rectangular slot. In the rim section, there are a plurality of elongate circumferentially oriented slots which are generally transverse to the longitudinal axis of the device. For example, the circumferentially oriented slots may be perpendicular to the longitudinal axis of the device. Each slot is surrounded by several struts including a plurality of circumferentially oriented struts, substantially transverse to the longitudinal axis and connected together with one or more connector element that is axially oriented and substantially parallel to the longitudinal axis of the device, thereby defining a rectangular slot. In the intermediate section, there are a plurality of elongate axially oriented slots which are generally parallel to the longitudinal axis of the device. Each slot is surrounded by several struts including a plurality of axially oriented struts, substantially parallel to the longitudinal axis and connected together with one or more circumferentially oriented connector elements thereby defining a rectangular slot. The struts in the intermediate region may be wider than the struts in either the flared region, or the rim region, or both, in order to create a more rigid region that does not radially expand as much as the flared region. Similarly, the length of the struts may be longer, or shorter, or adjusted to the struts in the flared region to control radial expansion. Optionally or additionally, in the flared region, the slots may be of a plurality of sizes with varying lengths and widths and therefore the slots may be the same or different.

In any example, slit-type coronary flow-modifying implant 1100 is designed to alter its shape in response to manipulation and/or expansion following installation. In any example, slits 1138 expand so that a narrow passage 1168 automatically attains a first diameter during installation. In any example, following installation of slit-type coronary flow-modifying implant 1100, a balloon catheter is introduced into narrow passage 1168 and inflated to press radially outward on narrow passage 1168. In any example, a pressure of between 7 and 8 atmospheres, or less than 7 or greater than 8 atmospheres, depending on the stiffness of the component materials, causes expansion slits 1138 to expand to a larger cross section. This causes narrow section 1168 to have a larger diameter than it had immediately following installation.

While not shown, some of the slits, for example slits 1138 may be oblique relative to the longitudinal axis of the implant, thus possibly requiring a different degree of force to expand and/or providing a twisting of the deployed implant. Providing opposing oblique slits may be used in any example to control foreshortening of the implant. Oblique slits may be used to bias the implant to foreshorten on expansion.

In any example, when flow-modifying implant 1100 is installed, little or no blood migrates through the walls of narrow passage 1168 and/or a flare 1160 to contact the walls of the coronary sinus. This may be achieved by a narrow configuration of the slits. Alternatively, or additionally, the length of the slits decreases near narrowing 1168.

In any example discussed herein, narrowing 1168 remains unexpanded or only partially expanded while one or more flares 1160 on either end may be expanded into engagement with the vessel walls to anchor the device. A typical coronary sinus may be 4 mm to 16 mm in diameter, therefore the flared ends of the implant may be expanded approximately 4 mm to 16 mm in diameter, although this is not intended to be limiting. The flared ends may be expanded to any size to engage and anchor the implant into the treatment area tissue. Similarly, the narrowing 1168 may have a diameter approximately 2 mm-4 mm in diameter in order to provide desired flow characteristics, although this is not intended to be limiting. Therefore, upon expansion, the narrowing 1168 may have a diameter 10%-50%, or 15%-45%, or 20%-40%, or 25%-35% of the flare diameter, although this is not intended to be limiting. In any example the narrow section may be 15%, 20%, 25%, 30%, 35%, 40%, or 45% of the flared diameter, although this is not intended to be limiting.

In any example, to achieve limitation and/or cessation of blood flow through the implant walls, the slits (e.g., not only slits 1102 and 1104 at the rim) are increased in number, while their width is modified. The viscosity of the blood impedes its flow through the decreased width of the slits while the increased number of slits may foster expansion of implant 1100. This may result in a net reduction in blood flow through the implant walls.

Alternatively, or additionally in any example, the slit width may be used to help define the device geometry. For example, slits (actually spaces) 1104 are wider than the other slits. If slits 1104 are made wider than slits 1102, a curved in rim may result.

Also shown is an optional design in which slits are arranged in alternating rows of long and short slits. Alternatively, or additionally in any example and as shown, the size and/or density of slits is larger near the rims than near the center of implant 1100. Alternatively, or additionally in any example and as shown, the length of the slits increases as a function of the distance from narrowing 1168.

As shown in FIG. 4D, the material of implant 1168 is distorted by the expansion. Alternatively, or additionally in any example, the slits are distorted and the material is distorted to conform to these distortions. For example, the short axial slit nearest the rim achieves a trapezoid rather than rectangular shape. In general, the expanded configurations are idealized, with an actual expanded shape possibly including step-like distortions caused by the discrete pattern of the slits in the implant.

Figure 5:
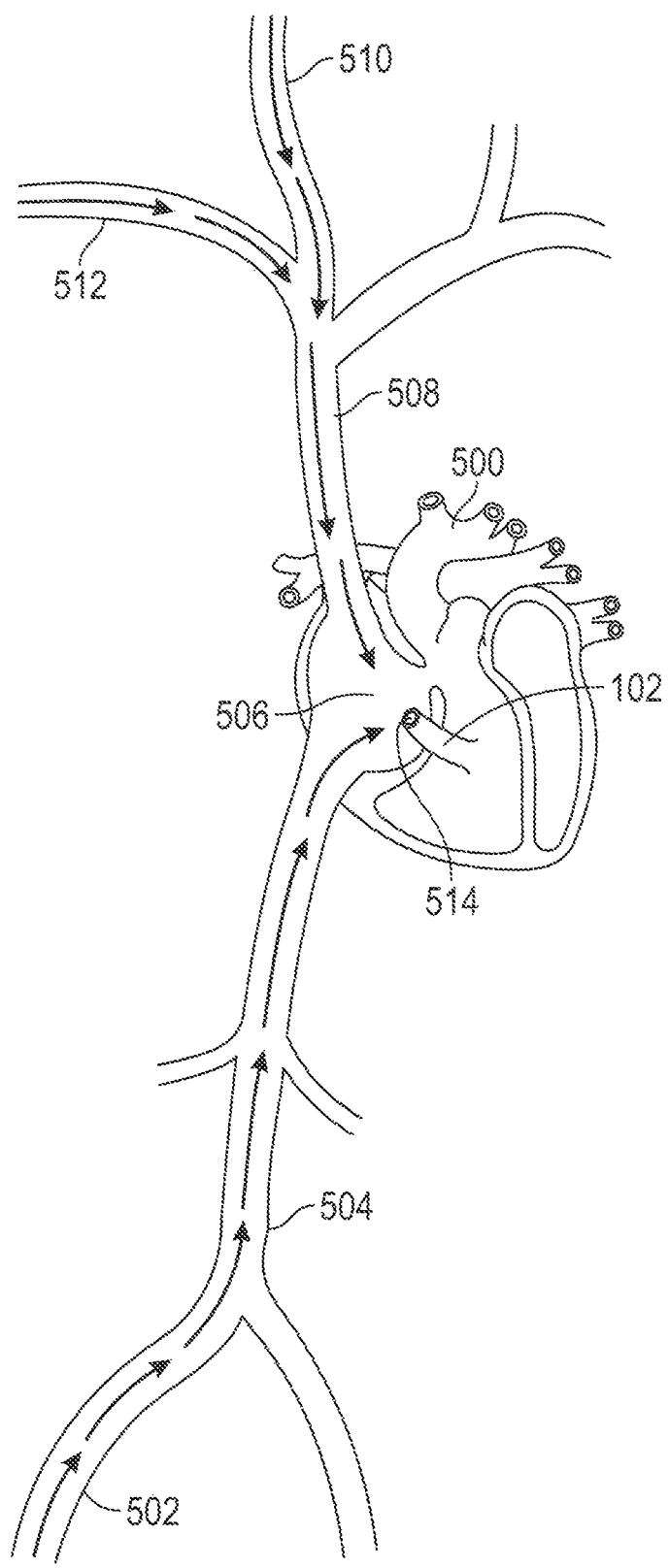
FIG. 5 is a vascular path to a coronary sinus.

FIG. 5 shows a vascular path to coronary sinus 102, which may be used with any example of flow modifying implant. The flow modifying implant 100 may be implanted using a trans-vascular approach, for example, from the venous system or by crossing through an intra-chamber wall in the heart. In any example of the method, the delivery system is inserted through a jugular vein 510 or a subclavian vein 512 to a right atrium 506 of a heart 500 via a superior vena cava 508 and/or a femoral vein 502, via an inferior vena cava 504. Once in right atrium 506, the delivery system is guided (e.g., through a sharp bend) to an opening 514 into coronary sinus 102. In some patients, a valve exists at the entrance to coronary sinus 102.

Figure 6:
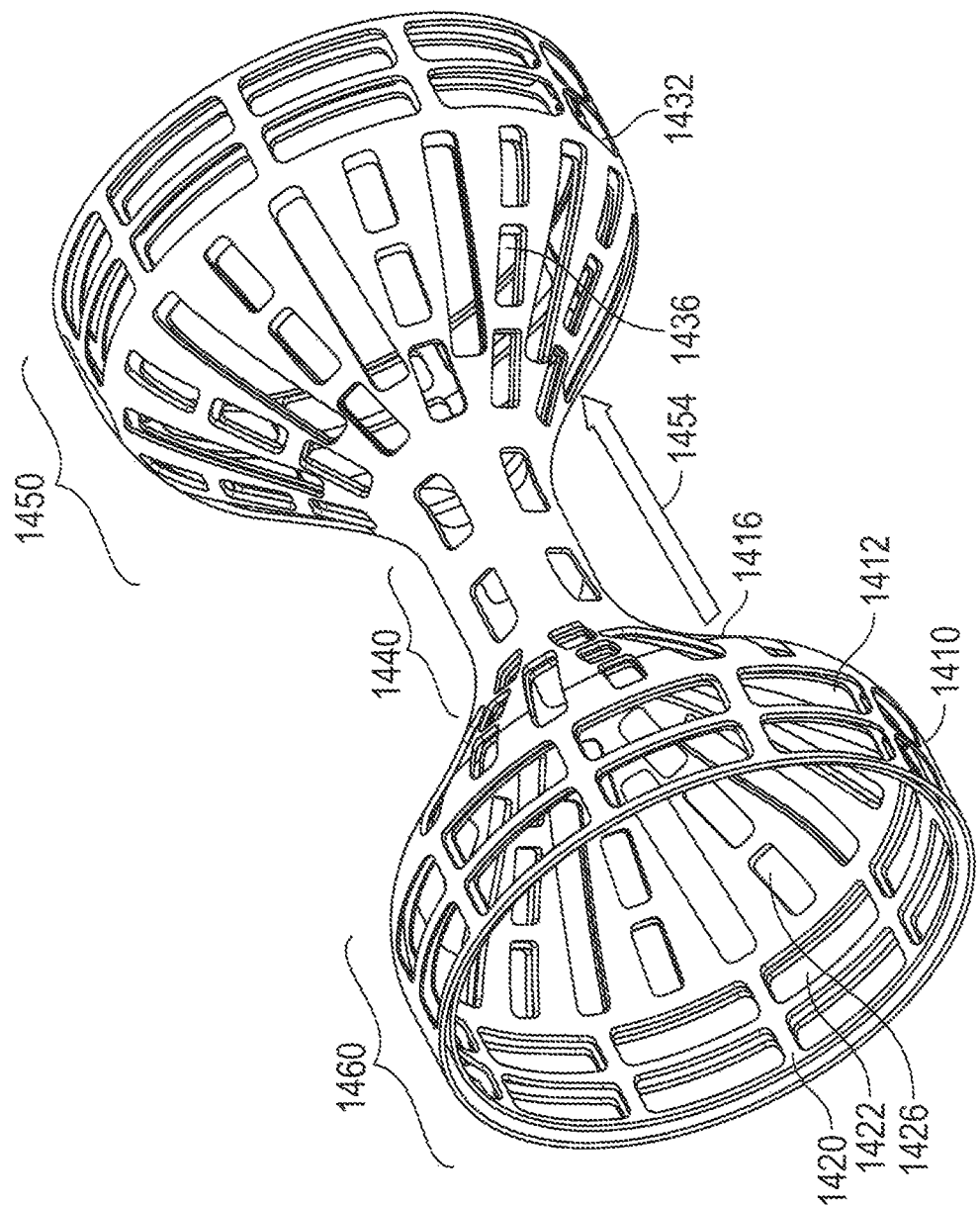
FIG. 6 is an isometric view of a dual layer flow modifying implant.

FIG. 6 is an isometric view of a dual layer flow-modifying implant 1400 In this example, dual layer flow-modifying implant 1400 comprises a first flared section 1450 and/or a second flared section 1460. For purposes of clarity, the components of flare 1460, alone, will be focused on, though similar features can be applied to flared section 1450.

In any example, dual layer flow-modifying implant 1400 comprises a flared section 1460 comprising an external cone 1420 and an internal cone 1410. For example, the dual layer flow-modifying implant may be formed by disposing any of the flow modifying implants disclosed herein inside a second flow modifying implant which may be any examples disclosed herein. Internal cone 1420, for example, comprises slits 1422 and 1426 and external cone 1410 comprises slits 1412 and 1416 so that cones 1410 and 1420 can be delivered to an implantation site in a non-expanded state and expanded at the implantation site. The flared portion of any example disclosed herein may be linear and monotonically increasing with or without a flat linear plateau section, or it may be a curved flare with a linear plateau section. The struts, slots, and cross sections generally take the same form as in FIG. 4D.

Further expansion of cone 1410 and/or 1420 may be desirable and can be incorporated into their respective designs so that cone 1410 and/or 1420 expand to a first diameter when pressed radially outward by a balloon catheter at a first expansion pressure. Cone 1410 and/or 1420 can then expand to a second, greater, diameter when pressed radially outward by a balloon catheter at a second, greater, expansion pressure.

In any example, when slits 1422 and 1426 are aligned circumferentially with slits 1412 and 1416 respectively, blood flows in a direction 1454 (e.g., in a space 132 shown in FIG. 1) and through slits 1432 and 1436. With alignment of slits 1412 with 1422 and/or slits 1416 with 1426, flow-modifying implant 1400 may be implanted into a vessel with a relatively slow flow speed and/or low pressure. For example, with implantation in the coronary sinus narrow area 1440 may fill with tissue (e.g. endothelialization) that aids in anchoring implant 1400 without risk of an embolism.

Alternatively, or additionally, as there is limited or cessation of flow into space 132 (best seen in FIG. 1), a clot may form in area 1440 and stabilizes in its position. Stabilized clot in area 1440 becomes incorporated into the surrounding tissue and against dual cone flow-modifying implant 1400 so that it is further stabilized in its position.

In any example, slits 1422 and 1426 can be rotated, prior to implantation, in relation to slits 1412 and 1416 so that blood flow in direction 1451 is substantially stopped to various degrees. With misalignment of slits 1422 and 1426, reducing implant 1400 may be implanted into a vessel with a relatively higher flow speed and/or higher pressure, for example a main trunk of an artery thereby protecting the patient against the dangers of embolism migration.

In any of the examples described herein, the flow modifying implant has flared ends with a larger cross-sectional area than the intermediate portion. Due to continuity of flow, the flow rate must be the same across the entirety of the flow modifying implant discussed herein. Therefore, due to the smaller cross-sectional area of the intermediate portion, there is a higher fluid velocity and a lower pressure in the intermediate portion thereby resulting in a lower velocity and higher pressure in the inflow and outflow regions of the flared ends.

The alignment of slits 1422 and 1426 is optionally set prior to implantation in a blood vessel in relation to slits 1412 and 1416, in order to establish a pre-defined blood flow pattern, and the two layers expanded or allowed to expand, together. To ensure that cones 1410 and 1420 remain fixed in position in relation to each other, cones 1410 and/or 1420 have, for example, may include in any example a friction surface interface and/or interdigitation. Alternatively, or additionally in any example, the two layers may be deployed in different ways, for example, the inner layer may be plastically deployed and the outer layer self-deployed. Possibly, the profile of the two layers does not match along its entire length. Alternatively, or additionally in any example, the outer layer is plastically deformed by a self-deploying inner layer (which self-deployment may also provide the friction for locking). Alternatively, or additionally in any example, cone 1420 may be rotated, for example using a suitable internal engaging catheter, after implantation.

The flared sections 1450 and 1460 may be symmetric or they need not be symmetric. For example, the implant may also select between flow blockage at one section, the other and optionally both. Flow only into space 132, may assist in clot formation. Flow only out of space 132 may assist in collapsing a surrounding blood vessel.

FIGS. 7A-7G illustrate various flow-modifying implant variations. While a sigmoid-like flare is shown, a linear or other flared design may also be provided.

Figure 7A:
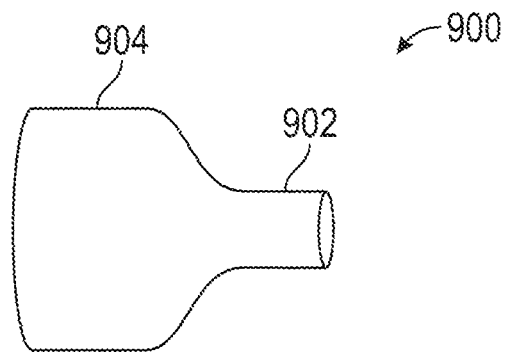
FIGS. 7A-7G are examples of flow modifying implants.

FIG. 7A is a flow-modifying implant 900 with having a narrowed section 902 and a single flared section 904. Narrowed section 902 may point upstream or downstream. One potential advantage of this design is that the delivery system is less likely to get caught inside narrowed section 902. Another potential advantage is that a completely obstructing implant can be provided. In any example however, even such a completely obstructing implant has smooth sides, to prevent damage to the coronary sinus. Possibly, the outer diameter of the completely obstructing implant or a nearly complete flow-modifying implant is increased beyond that of the coronary sinus, to prevent dislodgment of the implant. Alternatively, or additionally in any example, one or more barbs (not illustrated) on the outside of the implant may be provided. Optionally, a cone shaped flow-modifying implant is provided with one or more openings for blood flow on the face of the cone, rather than at its apex as shown. For example, there may be one or more apertures on the side wall of the device.

Alternately to a plain flow-modifying implant, the narrowing may be a valve, for example, a valve that opens, to a full or partial diameter, after a suitable pressure is achieved in the coronary sinus distal from the right atrium. For example, a leaflet valve or other type of vascular valve as known in the heart may be provided.

Figure 7B:
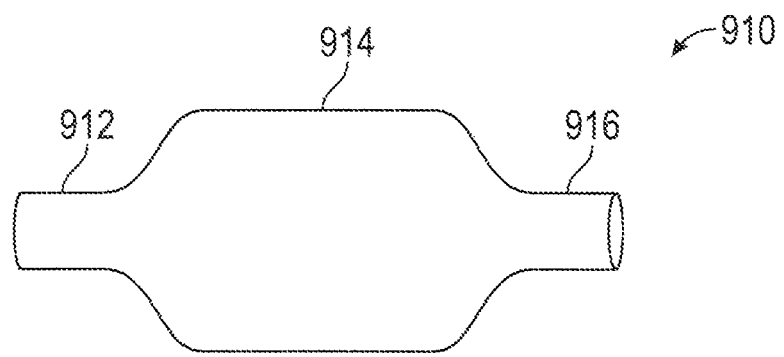

FIG. 7B shows an alternative flow-modifying implant 910; with two narrowed sections 912 and 916 sandwiching a flared section 914 between them. Optionally, the different narrowed sections have a different inner diameter so one may be larger than the other. Optionally, the narrowed sections are selectively expanded using a balloon to achieve a desired pressure profile.

Figure 7C:
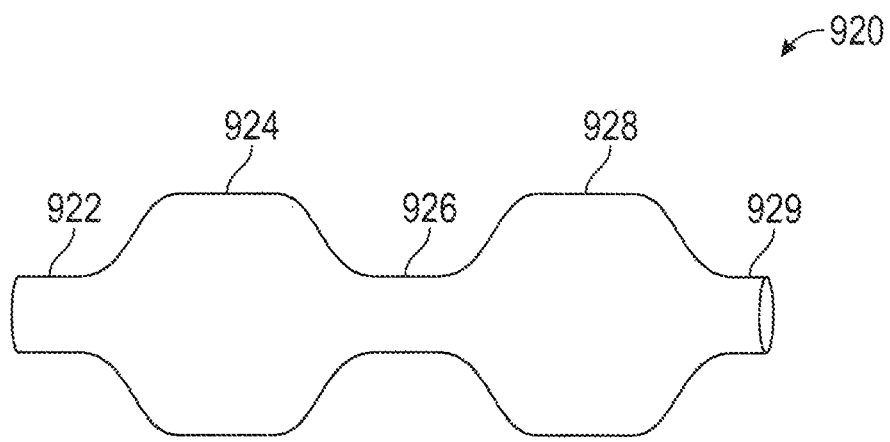

FIG. 7C is an alternative flow-modifying implant 920 with three narrowed sections 922, 926 and 929 and two flared sections 924 and 928 between the narrowed sections.

Figure 7D:
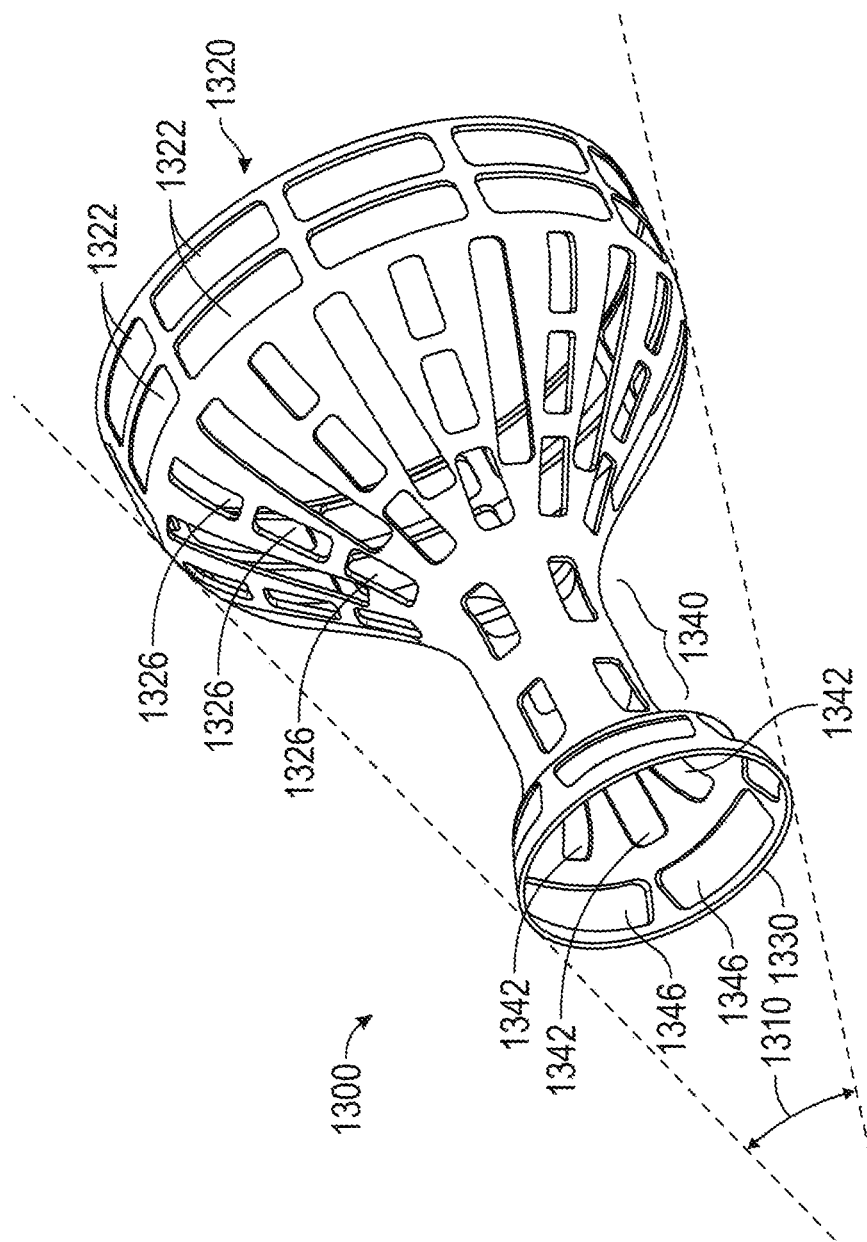

Certain blood vessels may exhibit a taper along their length, for example forming an angle 1310, shown in FIG. 7D. Vessels that change in size along their length may occur, for example, in the coronary sinus as it joins into the right atrium. In a tapered blood vessel, it may be desirable to utilize a tapered-type flow-modifying implant 930 (FIG. 7E), seen in detail in FIG. 7D, in accordance with examples of the implant.

FIG. 7D is an isometric view of an example of a tapered flow-modifying implant 1300, (with a similar configuration to implant 930). Tapered flow-modifying implant comprises a smaller flared section 1330, a narrowed section 1340 and larger flared section 1320. The size of smaller flared section 1330, for example, is governed one or more slits 1342 that are transverse to the axis of narrowed section 1340 and one or more slits 1346 that are substantially parallel to the longitudinal axis.

The size of larger section 1320 is governed, for example, by two or more slits 1322 that are transverse to the axis of narrowed section 1340 and/or two or more slits 1320 that are substantially parallel to the longitudinal axis.

Optionally, slits 1342, 1346, 1322 and/or 1326, may be varied in size and/or geometrical configuration to govern the shape of flared sections 1320 and/or 1330. Alternatively, or additionally in any example, slits 1342, 1346, 1322 and/or 1326 may be have various arrangements to provide different contours to flared sections 1320 and/or 1330 and/or narrowed section 1340.

While openings 1330 and 1320 are shown as being round, they may have a variety of configurations to conform to different vessel configurations as noted above. Further, the ratio between opening 1330 and 1320 may be varied to conform to any vessel diameter where flow modifying implant 1300 is implanted. As in other figures, the material of the implant is shown distorted, while in some examples, it may be the slits, possibly in addition to the material, which is distorted.

Figure 7E:
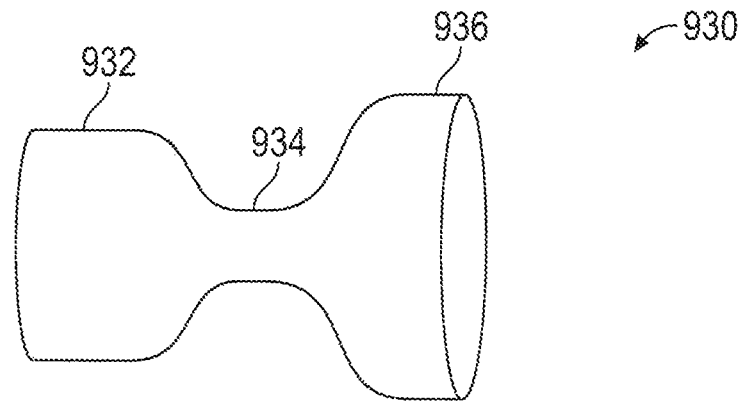

FIG. 7E is a tapered flow-modifying implant 930 in which one flared section 932 has a smaller diameter than a second flared section 936, but larger than an intermediate narrowed section 934.

Figure 7F:
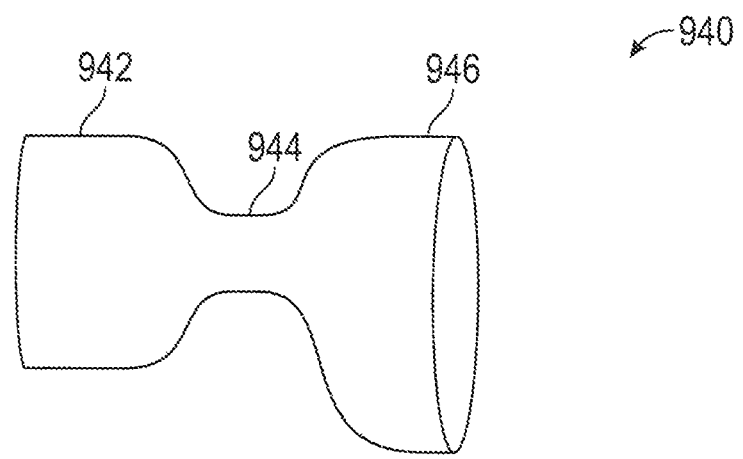

In FIG. 7F is a flow-modifying implant 940 that is not axially and/or rotationally symmetric around its axis. In any example, a first flared section 946 is distorted relative to an axis defined by a second flared section 942 and a narrowed section 944.

Optionally, flow-modifying implant 940 is curved. Here, asymmetric or curved flow-modifying implants include special markings, for example, radio-opaque or radio-transparent areas, to assist correct orientation of flow-modifying implant 940 in a blood vessel.

Figure 7G:
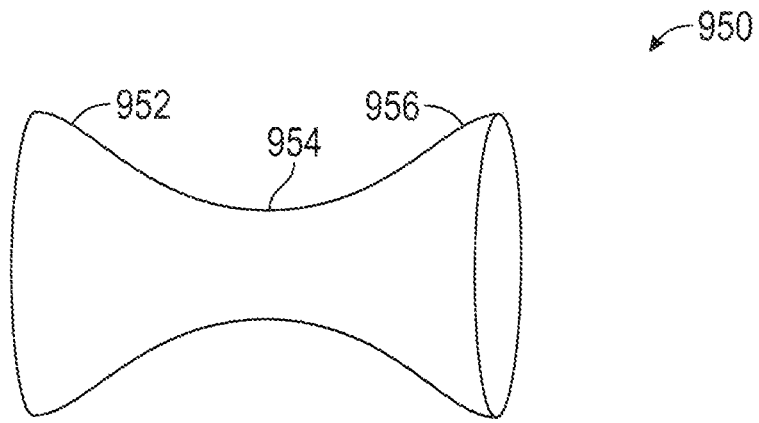

FIG. 7G is a flow-modifying implant 950, in which a narrowed section 954 is a sleeve 954. Sleeve 954, for example, is formed of a flexible graft material. Such as DACRON or GORTEX. Flow-modifying implant 950 further comprises at least one of two outer rings 952 and 956 that serve to anchor flow-modifying implant 950 in the blood vessel. A potential advantage of using a sleeve is that it can bend to conform to the vein geometry and/or dynamics. Other flow-modifying implant designs can also bend. Optionally, the graft material is elastic, so it can serve as a pressure limiting valve, to better control coronary sinus pressure. Optionally, a constraining ring is provided on the outside of section 954, to restrict the lumen of flow-modifying implant 950. Optionally, the ring is placed on flow-modifying implant 950 during the procedure, to achieve a desired narrowing effect. Alternatively, or additionally in any example, the ring is expandable, for example using a balloon, to allow controlling the narrowed section of flow-modifying implant 950. Optionally, the ring is sutured to narrowed section 954. Optionally, section 954 is stiffened, for example, using a wire, as known in the art of stent-grafts. The flow modifying implant may be any of the implants disclosed herein with a cover disposed thereover. In any example, the cover may be porous, semi-porous, or non-porous.

In any example, flow-modifying implant 100 is provided in kit form, possibly with a delivery system, a flow-modifying implant diameter control system, additional flow-modifying implants, external bands and/or other means for reducing its inner diameter and including instructions for use and/or size markings. Optionally, flow-modifying implant 940 is provided inserted into a delivery system or packaged with a delivery system.

As noted above, in any example, the flow modifying implant may be constrained by providing a band on the outside of the implant.

FIGS. 8A-8B are an isometric view and detail, respectively, of a ringed mesh-type flow modifying implant example. In any example, mesh-type flow modifying implant 1500 (FIG. 8A) comprises a flare shoulder 1502 and/or a flare shoulder 1504 that are relatively long in length, for example, to increase the area of contact between flow-modifying implant 1500 and surrounding vessel walls. Alternatively, or additionally in any example, tissue may grow through the mesh of flare shoulders 1502 and/or 1504, providing good anchorage of mesh-type flow-modifying implant 1500. Optionally, mesh-type flow-modifying implant 1500 comprises and/or is coated with materials that promote tissue ingrowth. A rim 1620, which may be, for example jagged (e.g. scalloped edge) or smooth is also optionally provided on each shoulder.

Optionally, the initial shape of mesh-type flow-modifying implant 1500 is governed by one or more bands 1522 and/or 1524 that constrict an area 1528 of mesh-type flow-modifying implant 1500. In any example, the surrounding tissue collapses onto mesh-type flow-modifying implant 1500 to modify blood flow through the walls of constriction area 1528. While two bands 1522 and 1524 are shown, a single band, for example band 1522 alone, may be used to create constriction area 1528.

In any example, an operator manually tying their ends together, prior to implantation, adjusts the rings formed by band 1522 and/or 1524 in circumference, for example. Adjustment of band 1522 and/or 1524 prior to implantation allows the operator to establish constriction area 1528 with a specific size to modify blood flow and thereby promote angiogenesis or otherwise redirect blood flow. Alternatively, or additionally in any example, a balloon catheter, for example, is expanded in area 1562 to cause expansion of bands 1522 and/or 1524, thereby expanding area 1562 to increase blood flow there through. In this fashion, blood modification through flow-modifying implant 1500 can be regulated prior to placement and/or following placement of flow-modifying implant 1500 in a blood vessel.

In any example, band 1524 may be fragile and rips when a large expansion force is placed against it. To adjust the diameter of area 1528 following implantation, a balloon catheter is positioned inside area 1562 and expanded until the pressure exceeds that which is required to rip band 1524. With band 1524 ripped, the area of mesh area 1562 directly under it expands so that area 1562 expands in diameter so that it has the diameter of ring 1522.

Optionally, in any example, band 1524 has a smaller diameter than band 1522, providing two levels of expansion. For example, so that as a balloon catheter is expanded to a first diameter, it expands smaller diameter band 1524, increasing the diameter of constriction area 1528 to a first expanded diameter. Should further increase in flow be desired, a balloon catheter is expanded to a second diameter and expands larger diameter band 1524 and/or smaller diameter band 1524, increasing the diameter of constriction area 1528 to a second expanded diameter.

Ring 1524 has, for example, a diameter of 6 millimeters while ring 1522 has a diameter of 8 millimeters so that area 1562 has flow passage of 6 millimeters. By expanding an expansion balloon inside area 1562 and causing ring 1524 to rip, the area under ring 1524 expands. However, ring 1522, with its diameter of 8 millimeters, maintains its integrity. Hence area 1562 now has a flow passage of 8 millimeters (less the thickness of the mesh or other material from which the implant is formed.

FIG. 8B is a detail of an example of ring 1522 comprising an adjustable band 1540 that forms ring 1522 and is held at a specific diameter by a clasp 1544. Alternatively, or additionally in any example, adjustable band 1540 is maintained at a specific diameter by a clasp 1546. In any example, clasps 1544 and/or 1546 hold adjustable band 1540 so that during implantation, ring 1522 remains at a specific diameter until, for example, an expanding balloon catheter is expanded against adjustable band 1540 and the diameter of ring 1522 is expanded. In any example, clips 1544 and 1546 comprise, for example, a nylon material that holds band 1522 at a specific diameter and allow expansion of the diameter only under expansion pressure from, for example, a balloon catheter. Optionally, two clasps are provided, so no part of band 1540 sticks out from the ring. In any example of the invention, the clasps are "C" shaped and band 1540 optionally include bumps that prevent sliding of the band through the clasps. Alternatively, or additionally in any example, friction prevents such sliding.

In any example, flare shoulders 1504 and/or 1502 are 0.5 centimeters to 1 centimeter in length through they could be less than 0.5 centimeters or greater than 1 centimeter in length, for example, depending upon vessel configuration.

In any example, mesh-type flow-modifying implant 1500 comprises strands that form its mesh comprising GORTEX, DACRON and/or steel. Further, the material comprising the mesh can be configured to be flexible or rigid, depending, for example, on the materials, its thickness, based upon, for example the flow dynamic dynamics desired.

Figure 9:
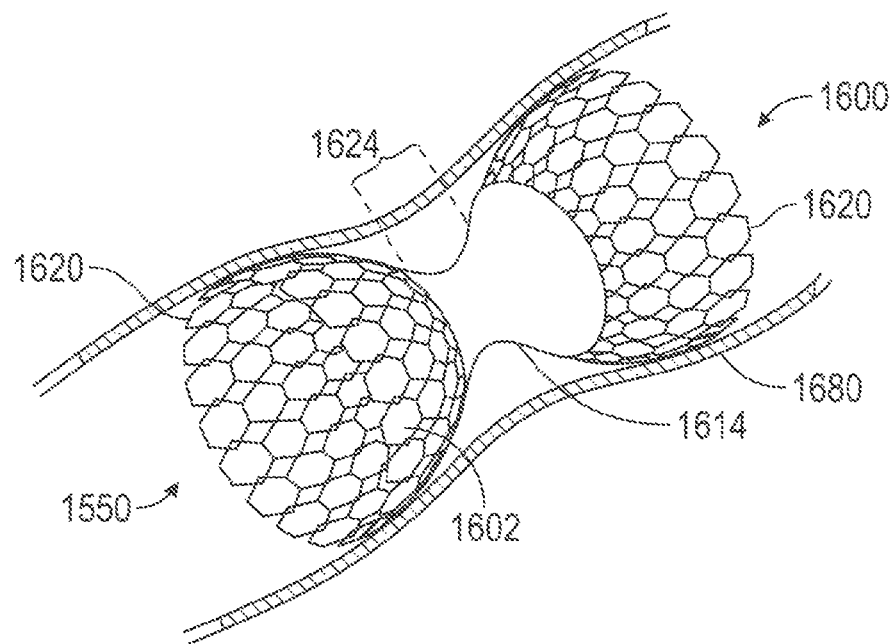
FIG. 9 is an isometric view of a partially covered mesh type flow modifying implant.

FIG. 9 is an isometric view of a partially covered mesh type flow modifying implant 1600. Mesh-type flow modifying implant 1600 comprises a covering 1614 over or inside narrow section 1624, implanted in a blood vessel 1680, shown in cross section. In any example, mesh-type flow modifying implant 1600 comprises one or more flare shoulders 1602 that contact blood vessel 1680 to provide anchoring. A rim 1620, which may be, for example jagged or smooth is also optionally provided on each shoulder.

Alternatively, or additionally in any example, mesh-type flow modifying implant 1600 comprises a covering 1614 that restricts blood flow through the wall surface of flow modifying implant 1600 and/or blood turbulence in an area of constriction 1624, thereby reducing danger of embolic migration problems.

In any example, covering 1614 comprises a separate, flexible layer, that is attached to flow modifying implant 1600 at several points (e.g., at constriction area 1624 and/or flare shoulders 1602) to prevent tearing when implant 1600 expands. Prior to expansion, for example, covering 1614 is folded and/or pleated. Alternatively, or additionally in any example, covering 1614 has a low bulk and, for example, is integrated into flow modifying implant 1600 structure, for example, so that it substantially spans the open areas of the mesh. Examples of materials comprising covering 1614, include GORTEX, latex and/or silicone, on the inside and/or outside of flow modifying implant 1600. Additional details about various configurations of the cover that may be applied to any example of a flow modifying implant disclosed herein are disclosed later in this application.

Figure 10:
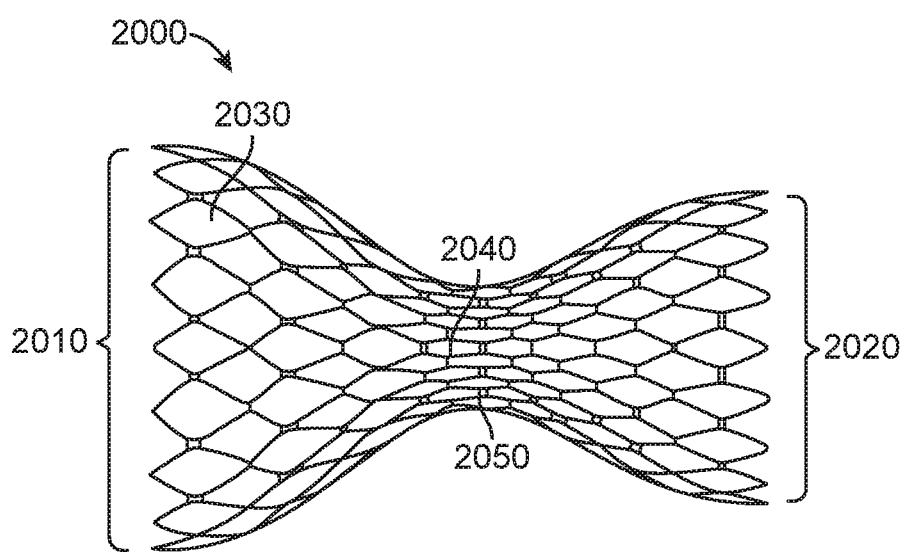
FIG. 10 illustrates an example of a flow and modifying implant.

FIG. 10 illustrates a flow modifying apparatus 2000 known in the art. It is a radially expandable implantable device. In some examples the device is formed from a plurality of connected struts 2040 and 2030. The struts are generally axially oriented and parallel with the longitudinal axis of the device. When the device is in its radially collapsed configuration, it has a low profile and may be delivered with a catheter to a target treatment site. The interconnected struts generally form a plurality of rectangular shaped cells 2040 with a rectangular window passing therethrough. When the device is radially expanded, the rectangular cells radially expand into diamond shaped cells 2030 at the proximal end 2010 and distal end 2020 of the device. In the middle section 2050 therebetween, the rectangular cells 2040 may remain substantially rectangular or they may form small diamond shaped cells depending on how much the middle section expands. The expanded diameter of the middle section 2050 may be any diameter but may be between 2 mm and 4 mm in diameter. Also, in any example, the cells in the proximal 2010 and distal ends 2020 have a length and a height. The height generally decreases from the proximal 2010 and distal ends 2020 inward toward the middle section 2050. Additionally, the length of the cells may decrease from the proximal 2010 and distal ends 2020 inward toward the middle section 2050 due to the foreshortening of the cells during radial expansion. Thus, the proximal 2010 and distal ends 2020 are generally flared to form trumpet shaped ends and may be monotonically increasing in diameter from the middle section 2050 outward toward the proximal or distal sections. The middle section 2050 has a significantly modified diameter relative to the expanded proximal and distal flared ends. Also, over the entire length of the device, the proximal 2010 or downstream end may have a larger diameter than that of the distal end 2020 or upstream end assuming placement in a coronary sinus retrogradely via the right atrium. In another example, the proximal 2010 or downstream end may have a smaller diameter than that of the distal end 2020 or upstream end, possibly if delivered in an antegrade direction. The larger diameter proximal end tapers to a modified diameter toward the center region where diameter may be minimal and then diameter increases toward the smaller diameter distal end. Or, described another way the diameter tapers down from either end of the apparatus toward the middle section. The proximal 2010 or distal end 2020 diameters can be either pre-determined sizes or made to expand to a variable size.

The flow modifying apparatus may be balloon expandable or it may be self-expanding. Once deployed in a body lumen, the larger diameter flared ends engage adjacent tissue and anchor the device to the vessel wall. The frame may be expanded 10% to 20%, or 10%-15%, or 15%-20% larger in size than the vessel diameter to help ensure proper engagement and embedding within the adjacent tissue. Fluid flows into the device and due to the smaller diameter middle region, cross sectional area decreases, and flow velocity is accelerated creating a pressure gradient across the device. Moreover, over time the device will become endothelialized and tissue will ingrow into or onto the metal struts of the device thereby further helping to anchor the device as well as to modify flow therethrough and establishing the pressure gradient across the device. The high back pressure may in fact force blood flow into other vessels which supply heart muscle which requires more blood supply thereby helping to alleviate ischemia and angina. Additionally, the pressure gradient creates a back pressure which also may help new blood vessel formation due to collateral opening, collateral formation, vasculogenesis and angiogenesis. In any example, the proximal end 2010 of the device which is closer to the right atrium has a larger diameter than the distal end of the device in order to accommodate the natural tapering of a lumen, such as in a blood vessel like the coronary sinus. However, one of skill in the art will appreciate that the proximal end 2010 may have the same diameter as the distal end 2020, or the distal end 2020 may have a larger diameter than the proximal end 2010. Further details about the pressure and flow modifying apparatus are disclosed in U.S. Pat. No. 9,364,354; the entire contents of which are incorporated herein by reference. Any aspects of the expandable frame in FIG. 10 of the present application may be applied to any example of a flow modifying implant described herein.

FIGS. 11A1, 11A2, and 11A3 illustrate several examples of covered flow modifying apparatuses. The covering allows instantaneous flow modification upon implantation unlike the uncovered example in FIG. 10 where tissue ingrowth takes time and therefore full modification of flow is not seen for several weeks until tissue ingrowth occurs. FIG. 11A1 includes a fully covered flow modifying apparatus. The radially expandable frame may be the same frame as disclosed in FIG. 10 above, a frame in U.S. Pat. No. 9,364,354 incorporated by reference, or any other frame disclosed herein or known in the art. In this example, the cover 2060 may be any material such as a fabric, a synthetic such as PTFE, ePTFE, DACRON, or any other polymer, or it may be any tissue such as pericardial or other biological tissue. The cover 2060 may be attached to the frame using sutures, adhesives, or any other techniques known in the art. The cover 2060 may be disposed on the outer surface of the frame, on the inner surface, only in the open cell regions, or any combination thereof. Having a fully covered device modifies flow immediately upon implantation and may alleviate angina right away.

The middle example seen in FIG. 11A2 illustrates a partially covered flow modifying apparatus. In this example, the middle section 2095 of the flow modifying apparatus remains uncovered while the flared ends have a proximal cover 2065 and a distal cover 2070. The ends of the frame in the flared regions may be fully covered or they remain partially uncovered as illustrated. An end of the proximal flared end may be uncovered 2090, or an end of the distal flared end may be uncovered 2080. This may have clinical advantages because the pressure gradient across the device will occur immediately after implantation, and so will be the anti-anginal and anti-ischemic effect which will start immediately after implantation of the device. In some instances, leaving the flared ends at least partially uncovered may be advantageous since having the bare metal struts of the device which are in direct contact with the vessel wall may have less of an inflammatory response than having the covered material engage the tissue.

The bottom illustration in FIG. 11A3 shows an example where the covered portion of the frame is only in the middle section 2100 and the upstream 2120 and downstream ends 2110 such as the flared trumpet ends remain uncovered so that bare metal engages the adjacent tissue. One of skill in the art will appreciate that the amount of covering may be adjusted in order to provide the desired flow velocity, pressure gradient or back pressure. In any example, the cover may cover the central ⅓, ½, or ⅔ of the apparatus. Other aspects of the examples shown in FIG. 11A may generally take the same form as disclosed elsewhere in this specification.

The sequence of sketches in FIGS. 11B1-11B3 illustrate a delivery system for a flow modifying apparatus. The top sketch in FIG. 11B1 shows a delivery catheter which may include an outer sheath 2130 and an inner shaft. The flow modifying device may be crimped or otherwise loaded onto the inner shaft and then the outer sheath is advanced over the flow modifying device to constrain it. In FIG. 11B2, the sheath 2130 is retracted once the apparatus is delivered to the desired target treatment site. This removes the constraint from the flow modifying apparatus allowing it to self-expand into the treatment site. The flared ends help anchor the apparatus into position. In FIG. 11B3, the sheath 2130 is fully retracted allowing full radial expansion of the flow modifying device 2140 into position. The catheter may then be removed from the patient leaving the flow modifying implant 2140 in the treatment region. This method of delivering the flow modifying implant may be used with any of the flow modifying apparatuses disclosed herein. In other examples of delivery systems, the delivery system may include an expandable member such as a balloon which is configured to balloon expand the flow modifying implant instead of self-expanding.

FIG. 11C illustrates another example of a flow modifying implant that generally takes the same form as in FIG. 10, except instead of a plurality of interconnecting struts, the implant is formed from a plurality of interwoven filaments that form a mesh which is then formed into the flow modifying apparatus, and which is generally the same as previously described in FIG. 10. The mesh may comprise of a narrow middle region 2050 and two flared region, a proximal flared region 2010 and a distal flared region 2020. It may be delivered using any of the methods disclosed herein and also has similar results on modifying flow and treating angina as previously disclosed.

FIG. 11D illustrates a flow modifying apparatus implanted into a blood vessel 2150. The flow modifying apparatus may be any of those disclosed herein and the blood vessel is the coronary sinus, the main vein which drains venous blood from the heart. As illustrated, the apparatus modifies flow through the device thereby forming a pressure gradient with a higher pressure upstream than downstream by utilizing a smaller diameter middle region 2165. As discussed previously this may create back pressure which helps redistribute the blood to more in-need areas of the heart muscle or may stimulate collateral blood vessel formation, or angiogenesis thereby alleviating angina. The proximal flared end 2160 may have a larger diameter than the distal flared end 2155, or the distal flared end 2155 may have a larger diameter than the proximal flared end 2160, or the proximal flared end 2160 and distal flared end 2155 may have the same diameter. The apparatus may be delivered using any of the delivery systems and methods disclosed herein.

Figure 12:
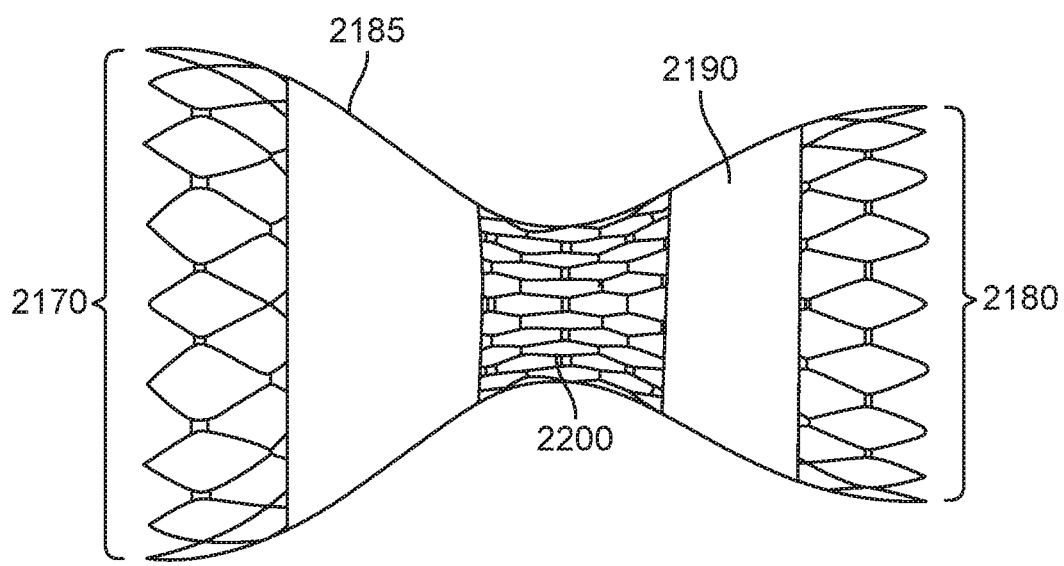
FIG. 12 illustrates an example of a flow modifying implant.

FIG. 12 illustrates an example of a flow modifying implant. The expandable frame is substantially the same as FIG. 10 but may be any of those disclosed herein. Covers 2185 and 2190 are then coupled to the frame at the proximal and distal ends. The cover may be any material including but not limited to fabric, a polymer, tissue or anything else. Examples of polymers include but are not limited to PTFE, ePTFE, DACRON, polyurethane, etc. Examples of tissue include but are not limited to pericardial tissue or other tissues. The middle section 2200 of the frame remains uncovered and the proximal 2170 and distal ends 2180 of the device also remain uncovered. Composite implants may be also be provided and implanted. For example, a plurality of rings or tubular elements may be coupled together to form a flow modifying implant. Each ring or tubular element may have a different geometry or structure or may be formed from a different material. For example, FIG. 12 may be modified so that cover 2190 may be different in material and structure from that of cover 2185 and there may or may not be a tubular support ring disposed under the sections. Additionally, covering 2190 or 2185 may not be porous and therefore there is no risk of blood flow through side apertures in these sections, and hence no "cover" is actually required. Alternatively, or additionally, covering 2190 and cover 2185 may not be covers, but part of the structure of the device. For example, covers 2190 and 2180 may be ring sections coupled together by middle section 2200 and also joined to the proximal-most and distal-most rings. Covers 2190 and 2180 acting as ring sections may be fabric, metal, or a combination thereof. Alternatively, or additionally, ring components 2180, 2200, and 2170 may be fabric, metal, or a combination thereof. The implant may comprise different materials and sections coupled together. For example, ring 2180 may be metal ring components coupled together to ring 2190 which may be a fabric component, coupled together with ring 2200 which may also be a metal component. In any example discussed herein, a material that forms the cover 2190, 2185 or composite ring section may be porous, semi-porous, or non-porous. Optionally, in any example, the cover 2190, 2185 may have discrete sections within a single ring that are porous, semi-porous, or non-porous so that the material has multiple properties. It should be understood that in any of these examples, a material forming the cover may itself comprise more than one material. In this example, the upstream end has a smaller flared diameter than the downstream flared diameter in order to accommodate the natural blood vessel taper. However, this not intended to be limiting and the upstream end may have a larger diameter or equivalent diameter than the downstream end. This flow modifying implant may be delivered using any of the delivery devices or methods disclosed herein, and other aspects of the device are generally the same as those described in FIG. 10.

Figure 15A:
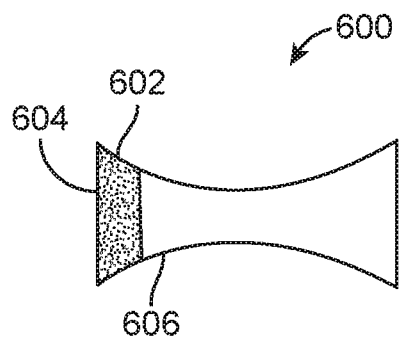
FIGS. 15A-15F illustrate examples of a flow modifying implant with a cover on various portions of the implant.

FIGS. 15A-15F illustrate examples of a cover disposed on the inflow or outflow end of a flow modifying device including any of those disclosed herein. In FIG. 15A, a cover 602 is disposed on the inflow end 606 of device 600. Here the cover 602 extends from the edge 604 of the inflow end toward the opposite end of the device but ends while on the tapered portion of the inflow end and does not extend past the midway point of the device along its longitudinal axis.

Figure 15B:
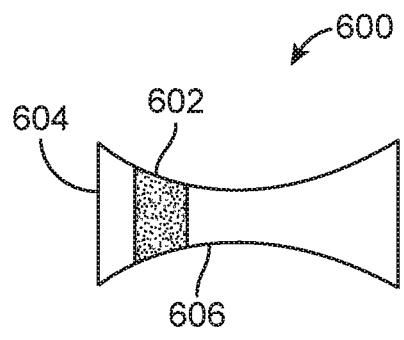

In FIG. 15B the cover 602 is still disposed on the inflow end 606 of the device 600, however, here the cover does not extend all the way to the edge of the inflow end and thus there the edge of the inflow end remains uncovered. The cover then extends toward the opposite end of the device but stops while still on the tapered portion of the inflow end and does not extend past the midway point of the device along its longitudinal axis.

Figure 15C:
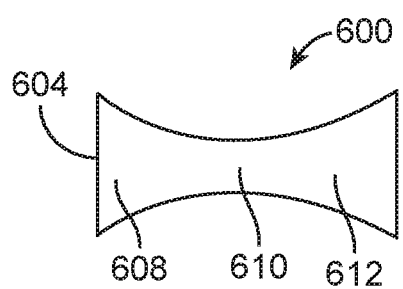

The cover may extend from any point on the inflow end and extend toward any point along the device. FIG. 15C shows that the cover may begin from the edge 604 of the inflow end of the device 600 or it may begin anywhere along the taper 608 and extend toward the midway point 610 the device along its longitudinal axis or even past 612 the midway point.

Figure 15D:
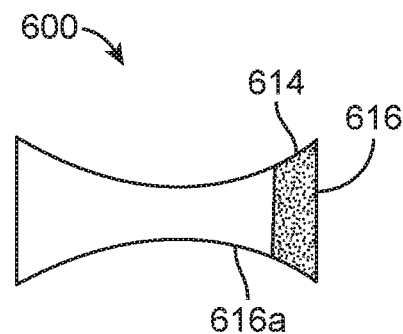

In FIG. 15D a cover 614 is disposed on an outflow of the device 600. It may begin from an edge 616 and extend toward the opposite end of the device but the terminating edge may still be on the tapered portion 616a of the outflow end.

Figure 15E:
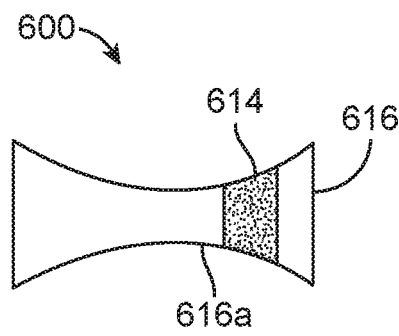

In FIG. 15E the cover 614 is disposed on the outflow end of the device 600 but the cover does not extend all the way to the edge 616 of the outflow end, and the opposite end extends toward the midpoint of the device along the device's longitudinal axis but ends while still on the tapered portion 616a of the outflow end.

Figure 15F:
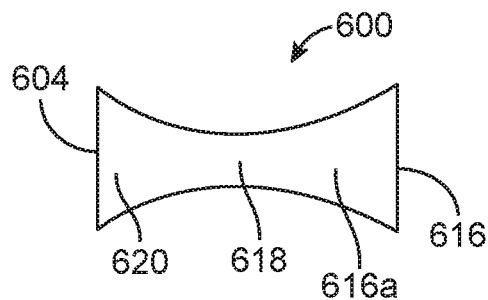

The cover may extend from any point on the outflow end of the device 600 as illustrated in FIG. 15F. For example, the cover may be disposed on the edge 616 of the outflow end or it may begin while on the tapered portion 616a of the outflow end and extend toward the midpoint 618 of the device along its longitudinal axis or may extend past 620 the midpoint.

In any of the examples disclosed herein, the cover may be a fabric such as DACRON, or a polymer such as silicone, or it may be tissue such as pericardial tissue. The cover may be coupled to the device with suture, adhesive, or other techniques known in the art.

Figure 13A:
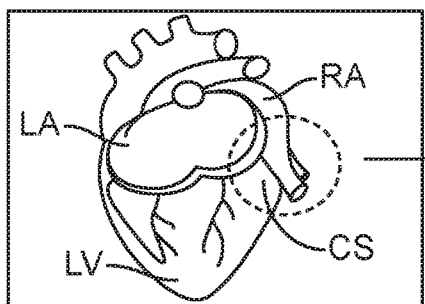
FIGS. 13A-13B illustrate basic human heart anatomy.
Figure 13B:
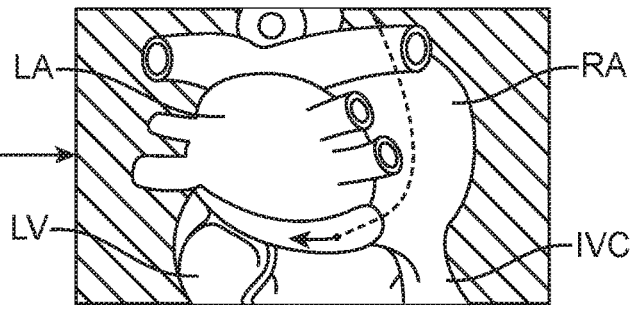

FIGS. 13A-13B illustrate basic human heart anatomy. In FIG. 13A the left atrium LA, right atrium RA, left ventricle are shown along with the coronary sinus CS. The coronary sinus is the main vein which drains venous blood from the heart.

FIG. 13B highlights the area around the left atrium LA and right atrium RA and left ventricle LV including the coronary sinus CS and inferior vena cava IVC.

Figure 14A:
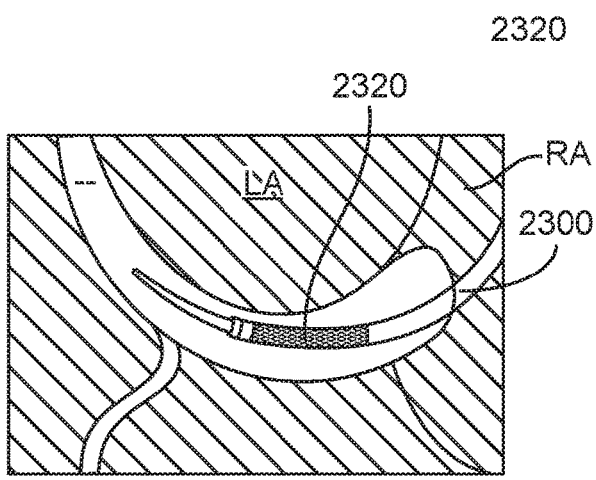
FIGS. 14A-14C illustrate an example of a method of delivering a flow modifying device to a treatment site.
Figure 14B:
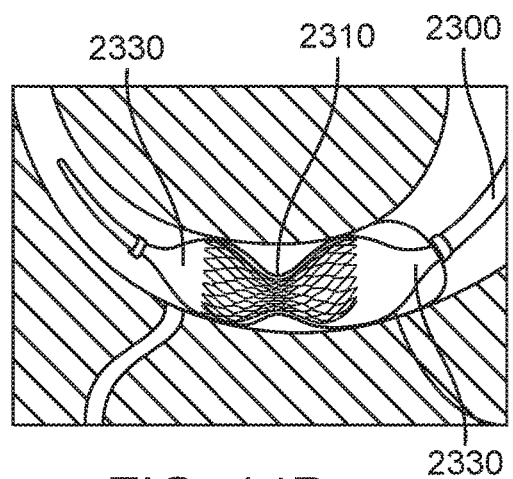
Figure 14C:
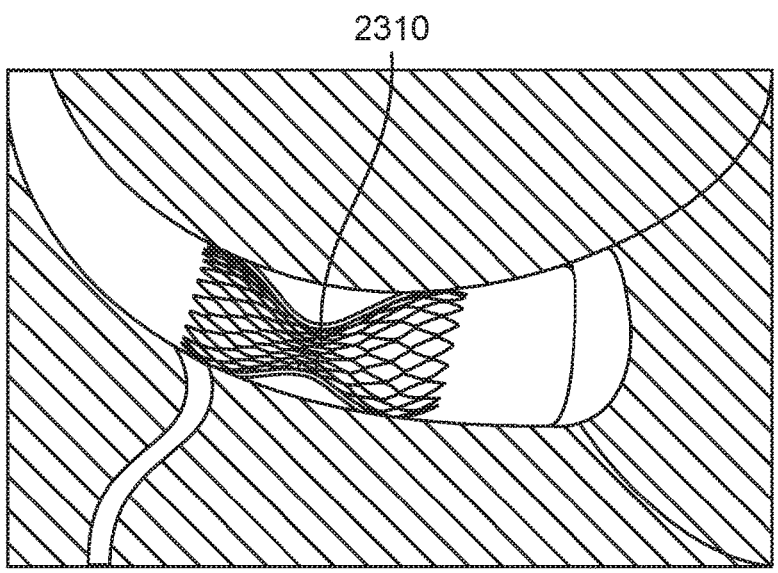

FIGS. 14A-14C illustrate an example of a method of delivering a flow modifying implant to the coronary sinus CS as a treatment for angina using any of the implants disclosed herein.

In FIG. 14A a delivery catheter 2300 such as any one of those disclosed herein is used to advance the flow modifying implant (any of those disclosed herein) to the coronary sinus CS. The delivery catheter 2300 has a crimped flow modifying implant 2320 coupled to the delivery catheter. The flow modifying implant may be any of those disclosed herein.

In FIG. 14B a balloon 2330 on the delivery catheter 2300 is radially expanded thereby expanding the flow modifying implant 2310. The flow modifying implant 2310 takes a similar size and shape as the balloon expanding the flow modifying implant 2310.

In FIG. 14C the balloon expands the flow modifying apparatus into engagement with the coronary sinus vessel walls. The balloon is then deflated and removed from the vessel thereby leaving the flow modifying apparatus 2310 at the target treatment site.

Any of the flow modifying apparatuses described herein may be balloon expandable or self-expanding. They may be placed in any target treatment region such as a blood vessel like the coronary sinus.

NOTES AND EXAMPLES

The following, non-limiting examples, detail certain aspects of the present subject matter to solve the challenges and provide the benefits discussed herein, among others.

Example 1 is a flow modifying apparatus comprising: a plurality of struts coupled together to form a radially expandable frame having a proximal and distal end, wherein the proximal and distal ends are radially expandable into expanded proximal and distal ends; a reduced diameter portion of the expandable frame disposed between the expanded proximal and distal ends, wherein the reduced diameter portion comprises a fluid flow through passage; and a cover disposed over at least a portion of the radially expandable frame, wherein the reduced diameter portion modifies fluid flow therethrough immediately upon implantation thereof and forms a pressure gradient between an inflow end and the reduced diameter portion.

Example 2 is the apparatus of Example 1, wherein the pressure gradient is greatest between an inflow end of the apparatus and the reduced diameter portion.

Example 3 is any of the apparatuses of Examples 1-2, wherein a velocity of the fluid flow is greatest in the reduced diameter portion.

Example 4 is any of the apparatuses of Examples 1-3, wherein the expanded proximal and distal ends are flared ends.

Example 5 is any of the apparatuses of Examples 1-4, wherein the radially expandable frame has an outer surface and wherein the cover is disposed over only a portion of the outer surface.

Example 6 is any of the apparatuses of Examples 1-5, wherein the radially expandable frame has an outer surface and wherein the cover is disposed over all of the outer surface.

Example 7 is any of the apparatuses of Examples 1-6, wherein the cover is disposed only over the reduced diameter portion.

Example 8 is any of the apparatuses of Examples 1-7, wherein the expanded proximal and distal ends remain at least partially uncovered.

Example 9 is any of the apparatuses of Examples 1-8, wherein the cover comprises a polymer, a fabric, a synthetic material, tissue, or combinations thereof.

Example 10 is any of the apparatuses of Examples 1-9, wherein the cover is disposed centrally over at least ⅔ of the expandable frame.

Example 11 is any of the apparatuses of Examples 1-10, wherein the cover is positioned over the reduced diameter portion such that when the flow modifying implant is radially expanded into engagement with a blood vessel, the cover does not directly contact the blood vessel thereby modifying or preventing an inflammatory reaction.

Example 12 is any of the apparatuses of Examples 1-11, The apparatus of claim 1, wherein the cover is configured to prevent or minimize an inflammatory response by a vessel wall.

Example 13 is any of the apparatuses of Examples 1-12, The apparatus of claim 1, wherein the reduced diameter portion comprises a diameter between 2 to 4 mm.

Example 14 is any of the apparatuses of Examples 1-13, wherein the plurality of struts form a plurality of rectangular slots when the expandable frame is in a collapsed configuration, and wherein the plurality of rectangular slots expand into diamond shapes when the expandable frame is in a radially expanded configuration, and wherein the diamond shapes have a height and a length, and wherein the height decreases from the proximal and distal ends toward a center point disposed therebetween.

Example 15 is any of the apparatuses of Examples 1-14, wherein the length decreases from the proximal and distal ends toward the center point.

Example 16 is any of the apparatuses of Examples 1-15, wherein the flow modifying apparatus is self-expanding or balloon expandable.

Example 17 is any of the apparatuses of Examples 1-16, further comprising an inflow end and an outflow end, and wherein the cover is disposed only on the inflow end, or only on the outflow end.

Example 18 is a system for delivering a flow modifying implant, said system comprising: the flow modifying implant of any of Examples 1-17; and a delivery catheter.

Example 19 is a method for modifying flow in a blood vessel, said method comprising: providing a flow modifying apparatus comprising proximal and distal ends; delivering the flow modifying apparatus to a target treatment region in the blood vessel; radially expanding the flow modifying apparatus such that the proximal and distal ends are larger in diameter than a reduced diameter portion disposed therebetween; immediately modifying blood flow through the flow modifying apparatus upon delivery of the flow modifying apparatus thereby forming a pressure gradient between an inflow end of the flow modifying apparatus and the reduced diameter portion, and wherein a cover disposed over the flow modifying apparatus facilitates the modification in blood flow.

Example 20 is the method of Example 19, further comprising causing a velocity of the fluid flow to be greatest in the reduced diameter portion.

Example 21 is any of the methods of Examples 19-20, wherein radially expanding the flow modifying apparatus comprises forming flared regions at the proximal and distal ends.

Example 22 is any of the methods of Examples 19-21, wherein radially expanding the flow modifying apparatus comprises expanding the cover, the cover disposed over only a portion of an outer surface of the flow modifying apparatus.

Example 23 is any of the methods of Examples 19-22, wherein radially expanding the flow modifying apparatus comprises expanding the cover, the cover disposed over all of an outer surface of the flow modifying apparatus.

Example 24 is any of the methods of Examples 19-23, wherein radially expanding the flow modifying apparatus comprises expanding the cover, the cover disposed over only the center region.

Example 25 is any of the methods of Examples 19-24, wherein radially expanding the flow modifying apparatus comprises expanding the cover, wherein the proximal and distal ends remain at least partially uncovered.

Example 26 is any of the methods of Examples 19-25, wherein radially expanding the flow modifying apparatus comprises expanding the cover without directly contacting the blood vessel thereby modifying or preventing an inflammatory reaction.

Example 27 is any of the methods of Examples 19-26, wherein radially expanding the flow modifying apparatus comprises forming diamond-shaped cells from rectangular shaped cells, and wherein a height of the diamond-shaped cells decreases from the proximal end and distal end toward a center point disposed therebetween.

Example 28 the method of any of the methods of Examples 19-27, wherein the diamond-shaped cells have a length and the length decreases from the proximal and distal ends toward the center point.

In Example 29, the apparatuses or methods of any one or any combination of Examples 1-28 can optionally be configured such that all elements of options recited are available to use or select from.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A flow modifying apparatus comprising:
   a plurality of struts coupled together to form a radially expandable frame having a proximal end portion and a distal end portion, wherein the proximal end portion and the distal end portion are radially expandable into expanded proximal and distal end portions, wherein the flow modifying apparatus extends from an inflow end of the radially expandable frame to an outflow end of the radially expandable frame;
   a reduced diameter portion of the expandable frame disposed between the expanded proximal end portion and the expanded distal end portion, wherein the reduced diameter portion comprises a fluid flow through passage; and
   a cover disposed over at least a portion of the radially expandable frame, the cover having an upstream terminus and a downstream terminus, the upstream terminus being spaced downstream from the inflow end of the radially expandable frame and the downstream terminus being spaced upstream of the reduced diameter portion of the radially expandable frame such that the cover is located only on a flared portion of the distal end portion, wherein the reduced diameter portion modifies fluid flow therethrough immediately upon implantation thereof and forms a pressure gradient between the inflow end and the reduced diameter portion of the apparatus.

2. The apparatus of claim 1, wherein the pressure gradient is greatest between the inflow end of the apparatus and the reduced diameter portion.

3. The apparatus of claim 1, wherein a velocity of the fluid flow is greatest in the reduced diameter portion.

4. The apparatus of claim 1, wherein the radially expandable frame has an inner surface and wherein the cover is disposed over only a portion of the surface such that portions of the radially expandable frame not adjacent the cover are uncovered to allow blood flow therethrough.

5. The apparatus of claim 1, wherein the radially expandable frame has an outer surface and wherein the cover is disposed over only a portion of the outer surface such that portions of the radially expandable frame not adjacent the cover are uncovered to allow blood flow therethrough.

6. The apparatus of claim 5, wherein the cover extends over 40% of a length of the flow modifying apparatus or less.

7. The apparatus of claim 1, wherein the cover comprises a polymer, a fabric, a synthetic material, tissue, or combinations thereof.

8. The apparatus of claim 1, wherein the cover is configured to prevent or minimize an inflammatory response by a vessel wall.

9. The apparatus of claim 1, wherein the reduced diameter portion comprises a diameter between 2 to 4 mm.

10. The apparatus of claim 1, wherein the plurality of struts form a plurality of rectangular slots when the expandable frame is in a collapsed configuration, and wherein the plurality of rectangular slots expand into diamond shapes when the expandable frame is in a radially expanded configuration, and wherein the diamond shapes have a height and a length, and wherein the height decreases from the proximal and distal ends toward a center point disposed therebetween.

11. The apparatus of claim 10, wherein the length decreases from the proximal and distal end portions toward the center point.

12. The apparatus of claim 1, wherein the flow modifying apparatus is self expanding or balloon expandable.

13. The apparatus of claim 1, wherein the cover forms a conical shape from the upstream terminus to the downstream terminus such that a diameter of the upstream terminus is larger than a diameter of the downstream terminus.

14. The flow modifying apparatus of claim 1, wherein a proximal-most edge of the outflow end has a larger diameter than a distal-most edge of the inflow end.

15. The apparatus of claim 14, wherein the expanded proximal and distal end portions are flared portions and the radially expandable frame forms a continuously curved body from the proximal-most edge to the distal-most edge such that the reduced diameter portion is tangent to a central longitudinal axis of the flow modifying device.

16. A system for delivering a flow modifying implant, said system comprising:
   the flow modifying implant of claim 1; and
   a delivery catheter.

17. Allow modifying apparatus comprising:
   a plurality of struts coupled together to form a radially expandable frame having a proximal end portion and a distal end portion, wherein the proximal end portion and the distal ends portion are radially expandable into expanded proximal and distal end portions, wherein the flow modifying apparatus extends from an inflow end of the radially expandable frame to an outflow end of the radially expandable frame;
   a reduced diameter portion of the expandable frame disposed between the expanded proximal end portion and the expanded distal ends portion, wherein the reduced diameter portion comprises a fluid flow through passage; and a cover having an upstream terminus and a downstream terminus located on the distal end portion;

wherein the reduced diameter portion modifies fluid flow therethrough immediately upon implantation thereof and forms a pressure gradient between the inflow end and the reduced diameter portion of the apparatus; and wherein the outflow end has a larger diameter than the inflow end.

18. The flow modifying apparatus of claim 17, wherein the cover is located only on a flared portion of the distal end portion and such that the cover forms a continuous conical shape all the way from the upstream terminus to the downstream terminus.

19. The flow modifying apparatus of claim 17, wherein a proximal-most edge of the outflow end has a larger diameter than a distal-most edge of the inflow end.

* * * * *